(12) United States Patent
Kuyler

(10) Patent No.: US 10,188,526 B2
(45) Date of Patent: Jan. 29, 2019

(54) SPINAL IMPLANT SYSTEM AND METHOD

(71) Applicant: Warsaw Orthopedic, Inc., Warsaw, IN (US)

(72) Inventor: Adriaan J. Kuyler, Memphis, TN (US)

(73) Assignee: Warsaw Orthopedic, Inc., Warsaw, IN (US)

(*) Notice: Subject to any disclaimer, the term of this patent is extended or adjusted under 35 U.S.C. 154(b) by 474 days.

(21) Appl. No.: 14/923,190

(22) Filed: Oct. 26, 2015

(65) Prior Publication Data
US 2017/0112631 A1    Apr. 27, 2017

(51) Int. Cl.
*A61F 2/44* (2006.01)
*A61F 2/46* (2006.01)
*A61F 2/30* (2006.01)

(52) U.S. Cl.
CPC .......... *A61F 2/447* (2013.01); *A61F 2/4455* (2013.01); *A61F 2/4611* (2013.01); *A61F 2002/30014* (2013.01); *A61F 2002/30018* (2013.01); *A61F 2002/30062* (2013.01); *A61F 2002/30065* (2013.01); *A61F 2002/30092* (2013.01); *A61F 2002/3093* (2013.01); *A61F 2002/30266* (2013.01); *A61F 2002/30405* (2013.01); *A61F 2002/30507* (2013.01); *A61F 2002/30515* (2013.01); *A61F 2002/30579* (2013.01); *A61F 2002/30841* (2013.01); *A61F 2002/4622* (2013.01); *A61F 2002/4627* (2013.01); *A61F 2310/00017* (2013.01); *A61F 2310/00023* (2013.01); *A61F 2310/00029* (2013.01); *A61F 2310/00071* (2013.01); *A61F 2310/00077* (2013.01); *A61F 2310/00179* (2013.01); *A61F 2310/00293* (2013.01); *A61F 2310/00359* (2013.01)

(58) Field of Classification Search
None
See application file for complete search history.

(56) References Cited

U.S. PATENT DOCUMENTS

| | | |
|---|---|---|
| 7,850,733 B2 | 12/2010 | Baynham et al. |
| 7,875,078 B2 | 1/2011 | Wysocki et al. |
| 7,909,869 B2 | 3/2011 | Gordon et al. |
| 8,062,375 B2 | 11/2011 | Glerum et al. |
| 8,105,358 B2 | 1/2012 | Phan |
| 8,105,382 B2 | 1/2012 | Olmos et al. |
| 8,123,810 B2 | 2/2012 | Gordon et al. |
| 8,133,232 B2 | 3/2012 | Levy et al. |
| 8,187,332 B2 | 5/2012 | Mcluen |
| 8,382,842 B2 | 2/2013 | Greenhalgh et al. |
| 8,394,145 B2 | 3/2013 | Weiman |
| 8,398,713 B2 | 3/2013 | Weiman |
| 8,403,990 B2 | 3/2013 | Dryer et al. |
| 8,435,298 B2 | 5/2013 | Weiman |

(Continued)

*Primary Examiner* — Sameh Boles

(57) ABSTRACT

A surgical instrument includes a first member and at least one lock. A second member includes at least one ramp that is translatable relative to the first member to engage and rotate the at least one lock relative to the first member between a locked orientation and a non-locked orientation with an interbody implant. The second member is engageable with the interbody implant to move at least a portion of the interbody implant between a contracted configuration and an expanded configuration. Implants, systems and methods are disclosed.

15 Claims, 30 Drawing Sheets

(56) References Cited

U.S. PATENT DOCUMENTS

| | | |
|---|---|---|
| 8,491,659 B2 | 7/2013 | Weiman |
| 8,518,120 B2 | 8/2013 | Glerum et al. |
| 8,523,944 B2 | 9/2013 | Jimenez et al. |
| 8,556,979 B2 | 10/2013 | Weiman et al. |
| 8,568,481 B2 | 10/2013 | Olmos |
| 8,628,577 B1 | 1/2014 | Jimenez |
| 8,628,578 B2 | 1/2014 | Miller et al. |
| 8,632,595 B2 | 1/2014 | Weiman |
| 8,663,329 B2 | 3/2014 | Ernst |
| 8,679,183 B2 | 3/2014 | Glerum et al. |
| 8,685,098 B2 | 4/2014 | Glerum et al. |
| 8,702,719 B2 * | 4/2014 | Refai ............... A61F 2/4611 606/99 |
| 8,709,086 B2 | 4/2014 | Glerum |
| 8,778,025 B2 | 7/2014 | Ragab et al. |
| 8,795,366 B2 | 8/2014 | Varela |
| 8,888,853 B2 | 11/2014 | Glerum et al. |
| 8,888,854 B2 | 11/2014 | Gierum et al. |
| 8,894,711 B2 | 11/2014 | Varela |
| 8,894,712 B2 | 11/2014 | Varela |
| 8,926,704 B2 | 1/2015 | Glerum |
| 8,940,049 B1 | 1/2015 | Jimenez |
| 9,039,771 B2 | 5/2015 | Glerum et al. |
| 9,119,730 B2 | 9/2015 | Glerum et al. |
| 2011/0054621 A1 | 3/2011 | Lim |
| 2011/0172721 A1 | 7/2011 | Varela |
| 2011/0172774 A1 | 7/2011 | Varela |
| 2012/0035729 A1 | 2/2012 | Glerum et al. |
| 2012/0109319 A1 | 5/2012 | Perisic |
| 2012/0150304 A1 | 6/2012 | Glerum et al. |
| 2012/0150305 A1 | 6/2012 | Glerum et al. |
| 2012/0158146 A1 | 6/2012 | Glerum et al. |
| 2012/0158147 A1 | 6/2012 | Glerum et al. |
| 2012/0158148 A1 | 6/2012 | Glerum et al. |
| 2013/0144388 A1 | 6/2013 | Emery et al. |
| 2013/0158664 A1 | 6/2013 | Palmatier et al. |
| 2014/0121774 A1 | 5/2014 | Glerum et al. |
| 2014/0324171 A1 | 10/2014 | Glerum et al. |

\* cited by examiner

SPINAL IMPLANT SYSTEM AND METHOD

TECHNICAL FIELD

The present disclosure generally relates to medical devices for the treatment of musculoskeletal disorders, and more particularly to a surgical system that includes a spinal implant and a method for treating a spine.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, correction, discectomy, laminectomy and implantable prosthetics. As part of these surgical treatments, spinal constructs, such as, for example, bone fasteners, spinal rods and interbody devices can be used to provide stability to a treated region. For example, during surgical treatment, surgical instruments can be used to deliver components of the spinal constructs to the surgical site for fixation with bone to immobilize a joint. This disclosure describes an improvement over these prior technologies.

SUMMARY

In one embodiment, a surgical instrument is provided. The surgical instrument includes a first member and at least one lock. A second member includes at least one ramp that is translatable relative to the first member to engage and rotate the at least one lock relative to the first member between a locked orientation and a non-locked orientation with an interbody implant. The second member is engageable with the interbody implant to move at least a portion of the interbody implant between a contracted configuration and an expanded configuration. In some embodiments, implants, systems and methods are disclosed.

BRIEF DESCRIPTION OF THE DRAWINGS

The present disclosure will become more readily apparent from the specific description accompanied by the following drawings, in which.

DETAILED DESCRIPTION

Figure 1:
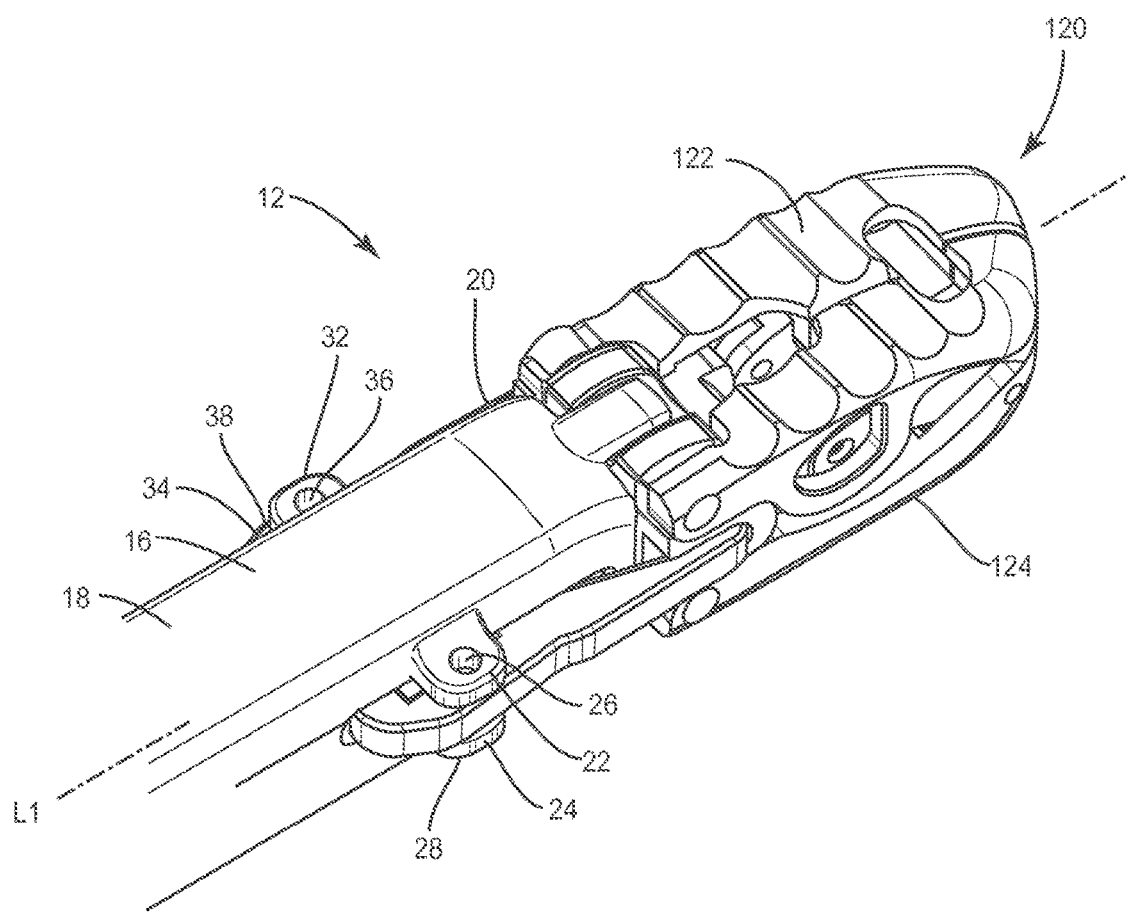
FIG. 1 is a break away perspective view of components of one embodiment of a spinal implant system in accordance with the principles of the present disclosure.

The exemplary embodiments of the surgical system and related methods of use disclosed are discussed in terms of medical devices for the treatment of musculoskeletal disorders and more particularly, in terms of a surgical system that includes a spinal implant and a method for treating a spine.

In some embodiments, the present system includes a surgical instrument comprising a grasping inserter configured for connection with an expandable interbody implant.

In some embodiments, the present system includes a surgical instrument comprising a grasping inserter configured for connection with a static interbody implant. In some embodiments, the surgical instrument includes a central rod, such as, for example, a driver configured to actuate arms disposed with the inserter. In some embodiments, the arms are configured to engage corresponding slots disposed with an interbody implant. In some embodiments, the present system is employed with a method such that as the driver is extended distally through the inserter, movement of the driver causes the arms to engage and grasp corresponding slots and/or holes defined in an interbody implant.

In some embodiments, the driver is configured for engagement with the interbody implant. In some embodiments, the driver includes a torx end configured to expand the interbody implant. In some embodiments, the surgical instrument includes a mating element, such as, for example, a projection configured to engage the interbody implant.

In some embodiments, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed spinal implant system may be alternatively employed in a surgical treatment with a patient in a prone or supine position, and/or employ various surgical approaches to the spine, including anterior, posterior, posterior mid-line, direct lateral, postero-lateral, and/or antero lateral approaches, and in other body regions. The present disclosure may also be alternatively employed with procedures for treating the lumbar, cervical, thoracic, sacral and pelvic regions of a spinal column. The spinal implant system of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, micro-discectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system including one or more spinal implants, related components and methods of employing the surgical system in accordance with the principles of the present disclosure. Alternate embodiments are disclosed. Reference is made in detail to the exemplary embodiments of the present disclosure, which are illustrated in the accompanying figures. Turning to FIGS. 1-5, there are illustrated components of a surgical system, such as, for example, a spinal implant system 10 including a surgical instrument 12.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, commercially pure titanium, titanium alloys, Grade 5 titanium, super-elastic titanium alloys, cobalt-chrome alloys, stainless steel alloys, super-elastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening dements and/or instruments, as described herein.

Spinal implant system 10 is employed, for example, with a minimally invasive procedure, including percutaneous techniques, mini-open and open surgical techniques to deliver and introduce instrumentation and/or one or more spinal implants at a surgical site within a body of a patient, for example, a section of a spine. In some embodiments, spinal implant system 10 may be employed with surgical procedures, as described herein, and/or, for example, corpectomy, discectomy, fusion and/or fixation treatments that employ spinal implants to restore the mechanical support function of vertebrae.

Surgical instrument 12 includes a handle (not shown) that is connected with a member, such as, for example, a tubular shaft 16. Shaft 16 extends between a proximal end 18 and a distal end 20. Shaft 16 defines a longitudinal axis L1. End 20 includes a pivot, such as, for example, flanges 22, 24 that are connected to a lock, such as, for example, an arm 50, as described herein. In some embodiments, shaft 16 can include one or a plurality of locks.

Flanges 22, 24 include openings 26, 28 configured to receive an element, such as, for example, a pin 30. Pin 30 facilitates rotation of arm 50 about flanges 22, 24 to engage an implant, such as, for example, an interbody implant 120, as described herein.

In some embodiments, end 20 includes a pivot, such as, for example, flanges 32, 34 that are connected to a lock, such as, for example, an arm 70, as described herein. Ranges 32, 34 include openings 36, 38 configured to receive an element, such as, for example, a pin 40 configured to facilitate rotation of arm 70 about flanges 32, 34 to engage interbody implant 120, as described herein. Ranges 22, 24, 32, 34 extend perpendicularly from shaft 16. In some embodiments, flanges 22, 24, 32, 34 may extend transverse and/or at other angular orientations such as acute or obtuse, co-axial and/or may be offset or staggered with respect to shaft 16.

Shaft 16 includes a surface 42 that defines a cavity 44. Cavity 44 is configured for disposal of a member, such as, for example, a drive rod 90, as described herein. Cavity 44 is configured for movable disposal of drive rod 90, as described herein, to facilitate engagement with interbody implant 120. In some embodiments, shaft 16 may have alternate cross section shapes, such as, for example oval, oblong, triangular, square, polygonal, irregular, uniform, non-uniform, offset, staggered, undulating, arcuate, variable and/or tapered.

Shaft 16 includes mating elements, such as, for example, projections 46 disposed at end 20. Projections 46 are configured for engagement with mating elements of interbody implant 120, as described herein. Projections 46 extend from shaft 16. In some embodiments, projections 46 may extend transverse and/or at other angular orientations such as acute or obtuse, co-axial and/or may be offset or staggered with respect to shaft 16. In some embodiments, shaft 16 includes one or a plurality of mating element engageable with an interbody implant. Engagement of projections 46 with interbody implant 120 stabilizes a connection between surgical instrument 12 and interbody implant 120. Engagement of projections 46 with interbody implant 120 facilitates engagement and disengagement of arms 50, 70 with interbody implant 120.

Arm 50 extends between an end 52 and an end 54. End 52 includes projections 56, 58 configured for slidable engagement with ramps 100, 102, as described herein, to facilitate rotation of arm 50 between a locked orientation and a non-locked orientation with interbody implant 120, as described herein. Projections 56, 58 extend from arm 50. In some embodiments, projections 56, 58 may extend transverse and/or at other angular orientations such as acute or obtuse, perpendicular, co-axial and/or may be offset or staggered relative to arm 50. Projection 56 is engageable with ramp 102 to bias arm 50 relative to shaft 16 and/or drive rod 90 in a direction into the locked orientation and projection 58 is engageable with ramp 100 to bias arm 50 relative to shaft 16 and/or drive rod 90 in an opposite direction into the non-locked orientation. In some embodiments, projections 56, 58 may be biased for rotation, pivoting, translation and/or lateral movement relative to shaft 16 and/or drive rod 90. In some embodiments, projections 56, 58 may be resiliently biased, such as, for example, with a biasing member such as a spring or elastic member.

End 52 includes a surface 60 that defines an opening 62 configured for disposal of pin 30, as described herein, to facilitate rotation of arm 50 relative to shaft 16. In some embodiments, opening 62 is disposed intermediate or at a midpoint between projections 56, 58. In some embodiments, opening 62 is disposed offset or staggered relative to projections 56, 58.

End 54 includes a mating element, such as, for example, a hook 64. Hook 64 extends from arm 50. In some embodiments, hook 64 may extend transverse and/or at other angular orientations such as acute or obtuse, perpendicular, co-axial and/or may be offset or staggered relative to arm 50. Hook 64 is configured for engagement with interbody implant 120 to facilitate insertion and orientation of interbody implant 120 at a surgical site.

Figure 2:
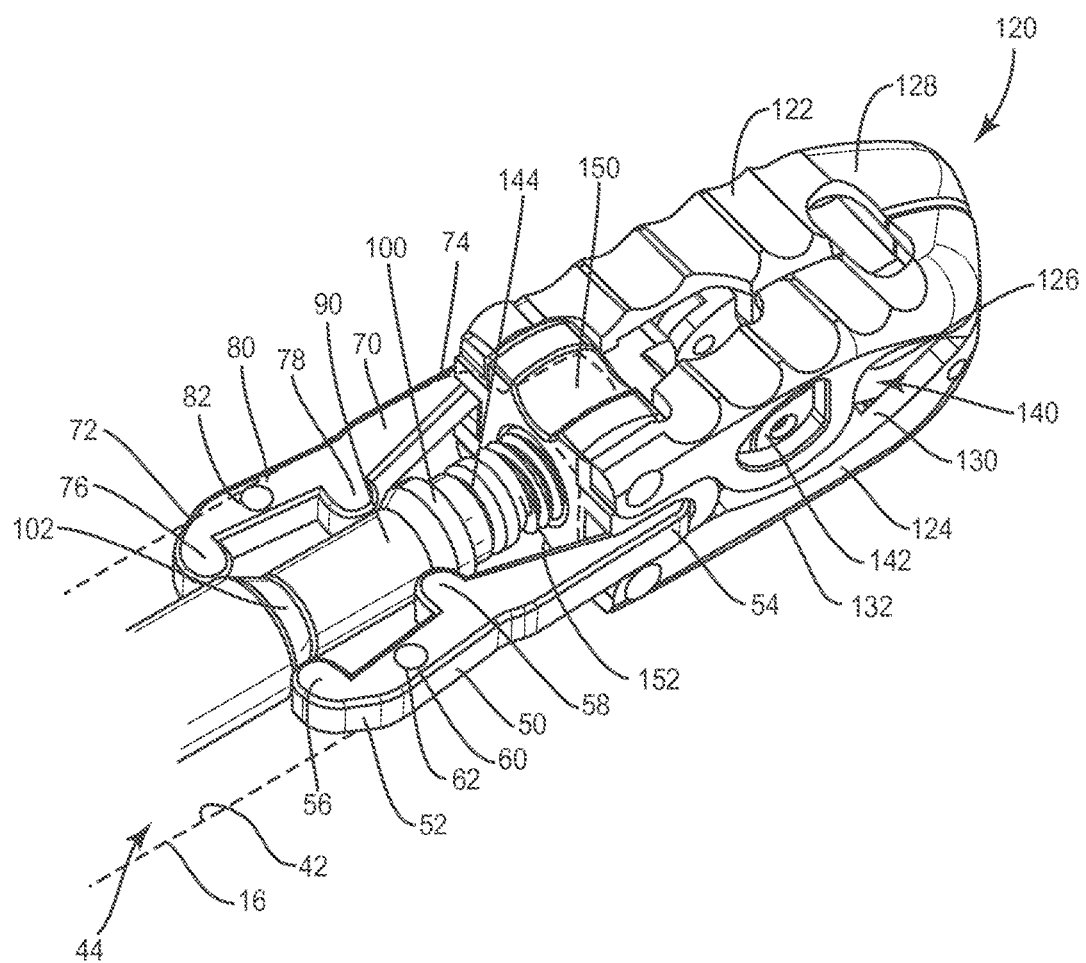
FIG. 2 is a perspective view, in part cutaway, of components of one embodiment of a spinal implant system in accordance with the principles of the present disclosure.
Figure 3:
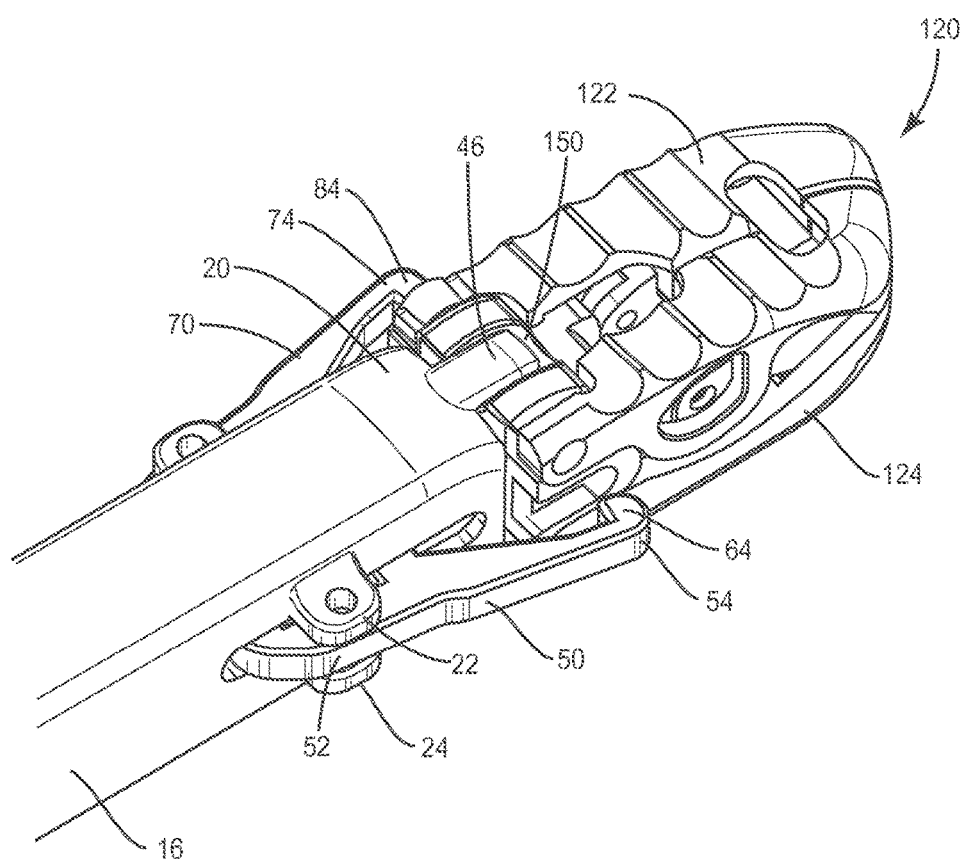
FIG. 3 is a perspective view of the components shown in FIG. 1.
Figure 4:
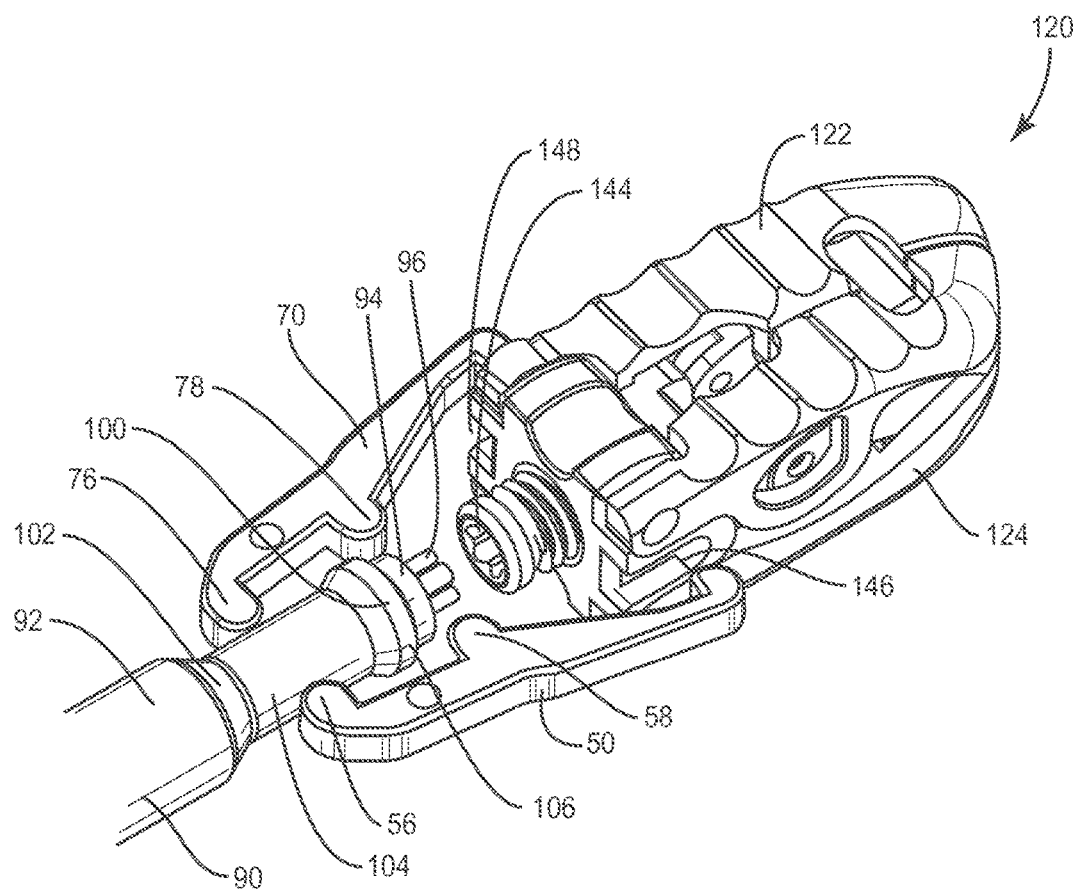
FIG. 4 is a perspective view, in part cutaway, of the components shown in FIG. 1.
Figure 5:
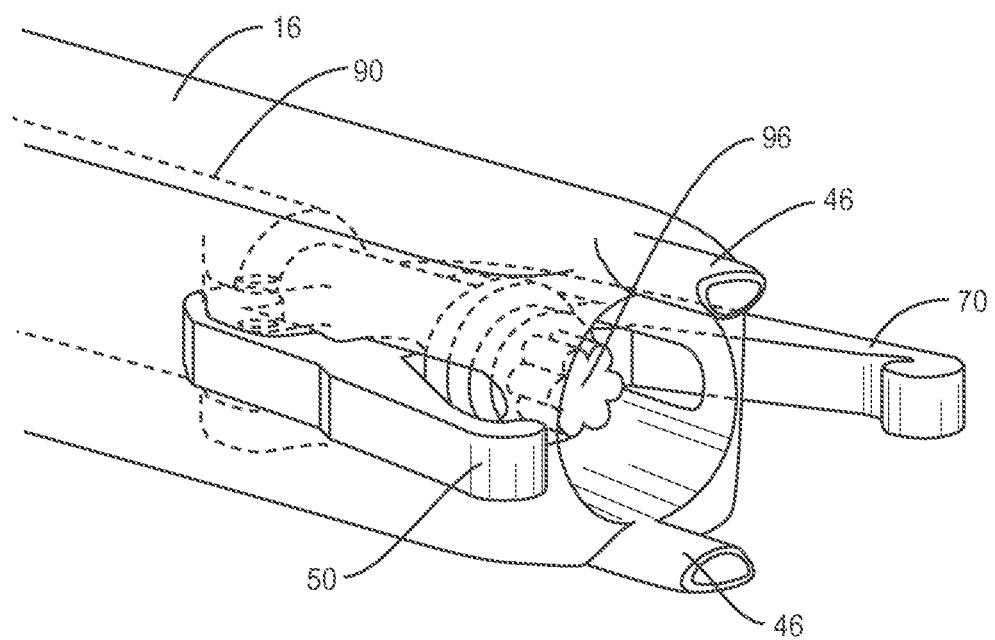
FIG. 5 is a perspective view, in part phantom, of components of the system shown in FIG. 1.
Figure 6:
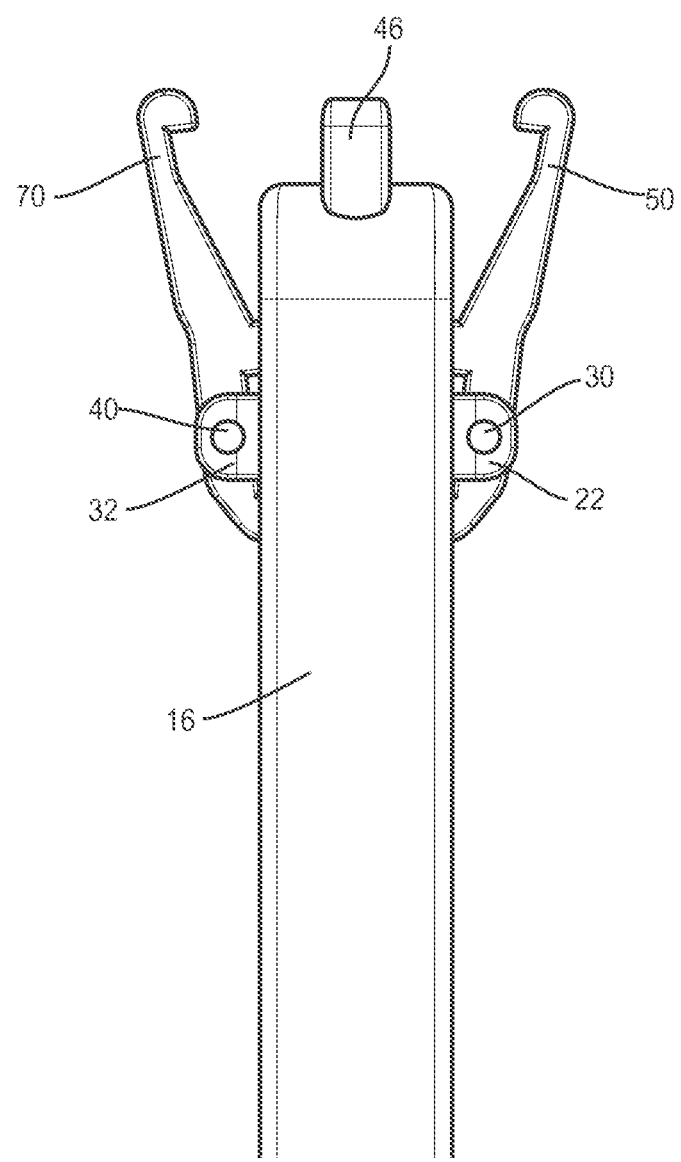
FIG. 6 is a plan view of components of the system shown in FIG.

Arm 70 extends between an end 72 and an end 74. End 72 includes projections 76, 78 configured for slidable engagement with ramps 100, 102, as described herein, to facilitate rotation of arm 70 between a locked orientation and a non-locked orientation with interbody implant 120, as described herein. Projections 76, 78 extend from arm 70 as shown in FIG. 2. In some embodiments, projections 76, 78 may extend transverse and/or at other angular orientations such as acute or obtuse, perpendicular, co-axial and/or may be offset or staggered with respect to arm 70. Projection 76 is engageable with ramp 102 to bias arm 70 relative to shaft 16 and/or drive rod 90 in a direction into the locked orientation and projection 78 is engageable with ramp 100 to bias arm 70 relative to shaft 16 and/or drive rod 90 in an opposite direction into the non-locked orientation. In some embodiments, projections 76, 78 may be biased for rotation, pivoting, translation and/or lateral movement relative to shaft 16 and/or drive rod 90. In some embodiments, projections 76, 78 may be resiliently biased, such as, for example, with a biasing member such as a spring or elastic member.

End 72 includes a surface 80 that defines an opening 82 configured for disposal of pin 40, as described herein, to facilitate rotation of arm 70 relative to shaft 16. In some embodiments, opening 82 is disposed intermediate or at a midpoint between projections 76, 78. In some embodiments, opening 82 is disposed offset or staggered relative to projections 76, 78.

End 74 includes a mating element, such as, for example, a hook 84. Hook 84 extends from arm 70. In some embodiments, hook 84 may extend transverse and/or at other angular orientations such as acute or obtuse, perpendicular, co-axial and/or may be offset or staggered with respect to arm 70. Hook 84 is configured for engagement with interbody implant 120 to facilitate insertion and orientation of interbody implant 120 at the surgical site.

Drive rod 90 extends between an end 92 and an end 94. End 92 is configured for engagement with an actuator, such as, for example, a surgical driver (not shown). End 94 includes an engagement portion 96 configured to engage a portion of interbody implant 120 to facilitate expansion and contraction of interbody implant 120, as described herein. In some embodiments, drive rod 90 is configured for engagement with interbody implant 120 to stabilize the connection of surgical instrument 12 with interbody implant 120. In some embodiments, engagement portion 96 includes configurations, such as, for example, triangular, square, polygonal, hexalobular, star or torx.

Drive rod 90 includes a surface 98. Surface 98 includes ramps, such as, for example, a ramp 100 and a ramp 102. Ramp 100 is oriented in spaced apart relation relative to ramp 102. An intermediate surface 104 is disposed between ramp 100 and ramp 102. Surface 104 is substantially even and circumferentially disposed about drive rod 90. Ramp 100 includes an apex 106. Ramp 102 includes an apex 108.

Drive rod 90 is configured to axially translate within cavity 44 relative to shaft 16 for engagement with interbody implant 120 to bias arms 50, 70 between a non-locked orientation and a locked orientation. In some embodiments, as drive rod 90 translates in a direction towards interbody implant 120, ramp 102 slidably engages projections 56, 76 to bias arms 50, 70 for rotation, about pins 30, 40 into engagement with interbody implant 120 into the locked orientation. Drive rod 90 is rotatable relative to shaft 16 to actuate expansion of interbody implant 120 between a contracted configuration and an expanded configuration, as described herein. In some embodiments, as drive rod 90 translates in a direction away from interbody implant 120, ramp 100 slidably engages projections 58, 78 to bias arms 50, 70 for rotation, about pins 30, 40 to disengage from interbody implant 120 into the non-locked orientation.

Figure 7:
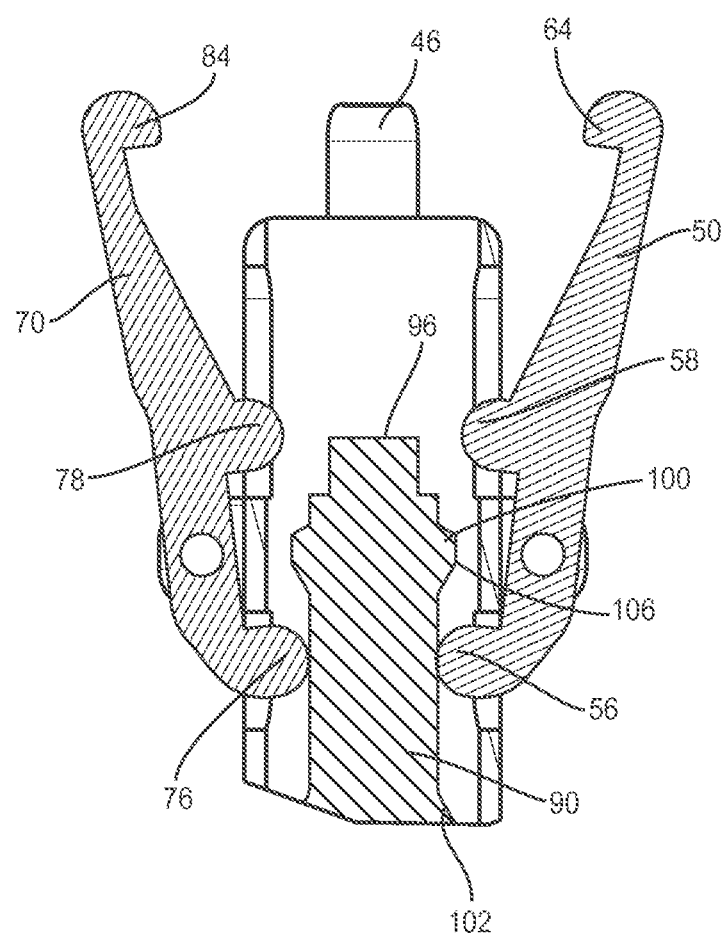
FIG. 7 is a cross section view of the components shown in FIG. 6.
Figure 8:
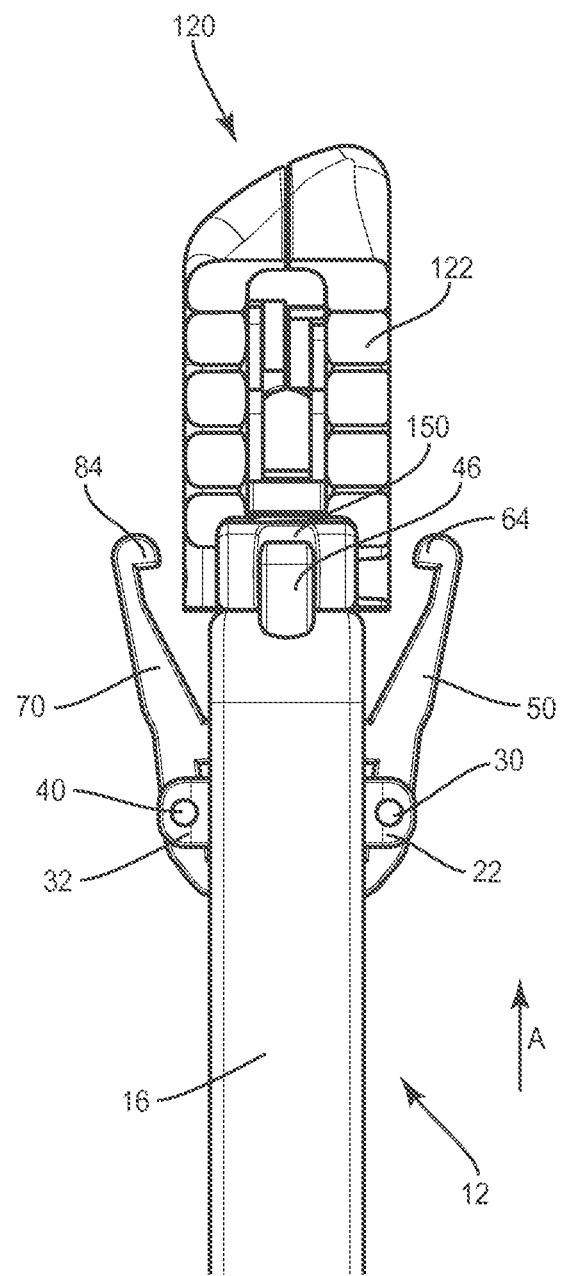
FIG. 8 is a plan view of components of one embodiment of a spinal implant system in accordance with the principles of the present disclosure.
Figure 9:
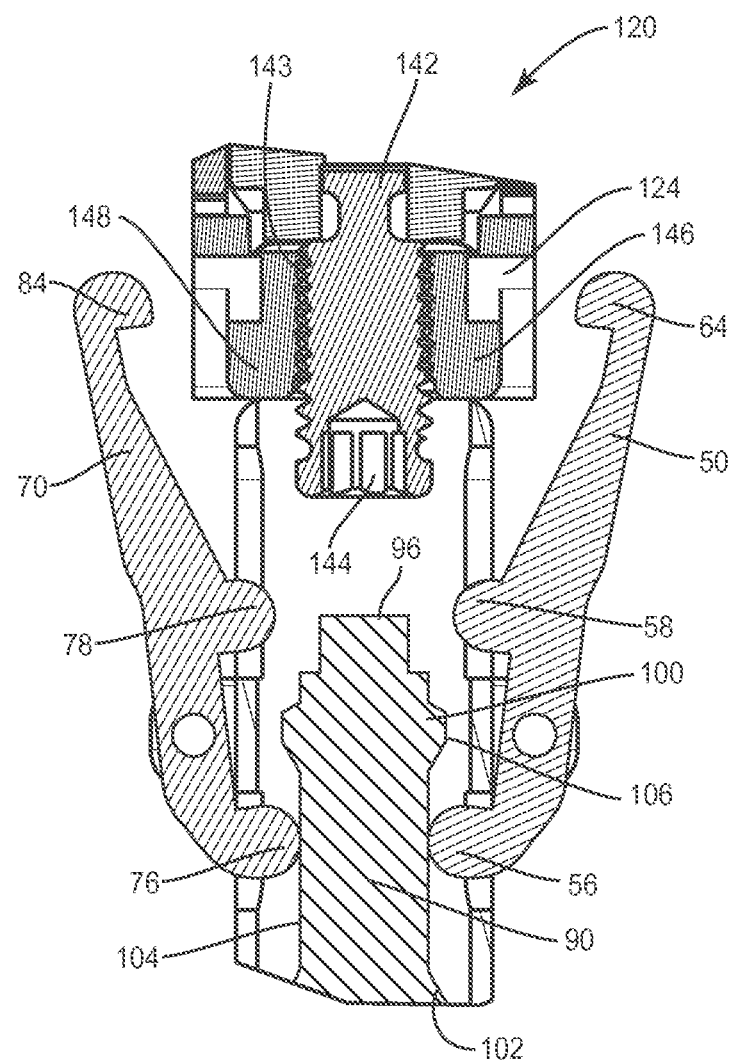
FIG. 9 is a cross section view of the components shown in FIG. 8.
Figure 10:
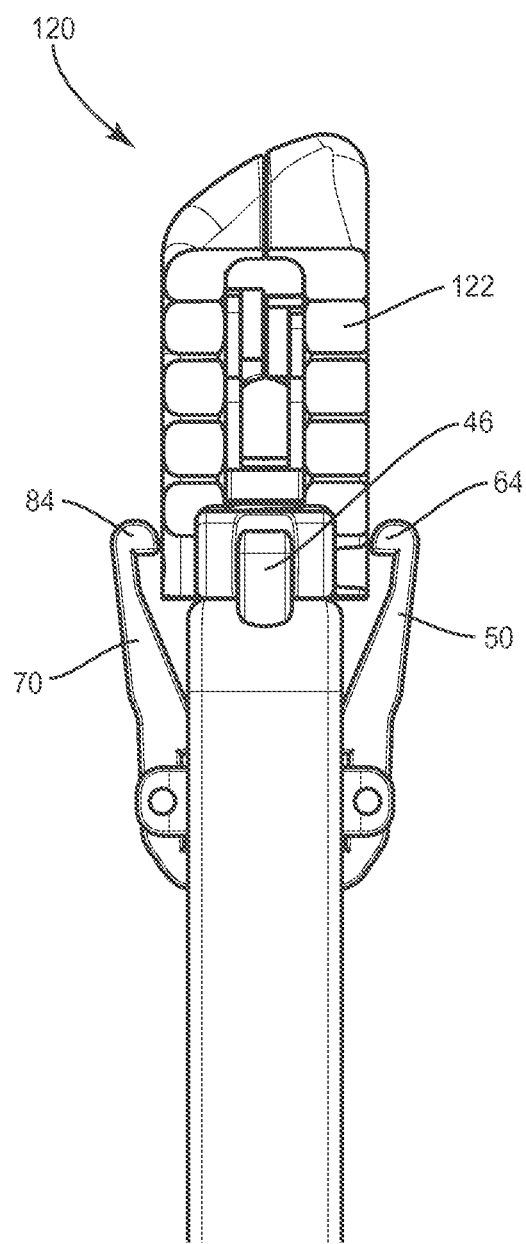
FIG. 10 is a plan view of components of one embodiment of a spinal implant system in accordance with the principles of the present disclosure.

In operation, for example, arms 50, 70 are disposed in an initial orientation, such as, for example, a non-locked orientation relative to interbody implant 120, as shown in FIG. 7. Drive rod 90 is translated in a direction towards interbody implant 120, in a direction shown by arrow A in FIG. 8, to engage interbody implant 120 and bias arms 50, 70 into a locked orientation. Translation of drive rod 90 causes ramp 102 to slidably engage projections 56, 76 to bias arms 50, 70 for rotation about pins 30, 40. Arms 50, 70 rotate about pins 30, 40 and into engagement with interbody implant 120 to dispose surgical instrument 12 with interbody implant 120 in a locked orientation.

Figure 11:
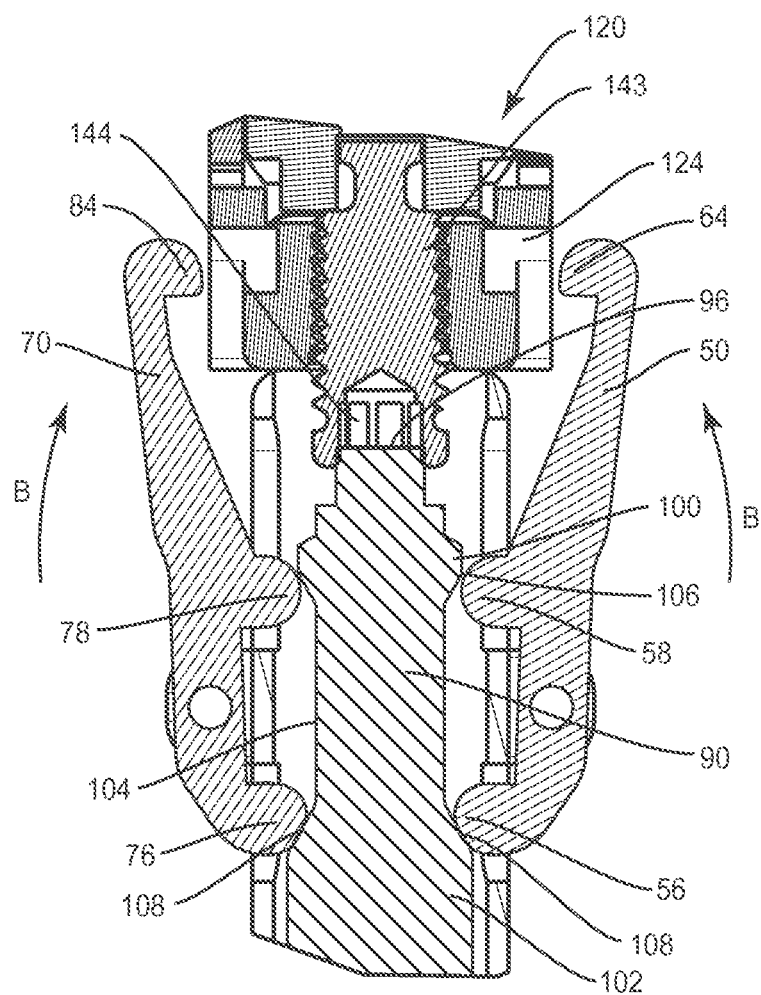
FIG. 11 is a cross section view of the components shown in FIG. 10.
Figure 12:
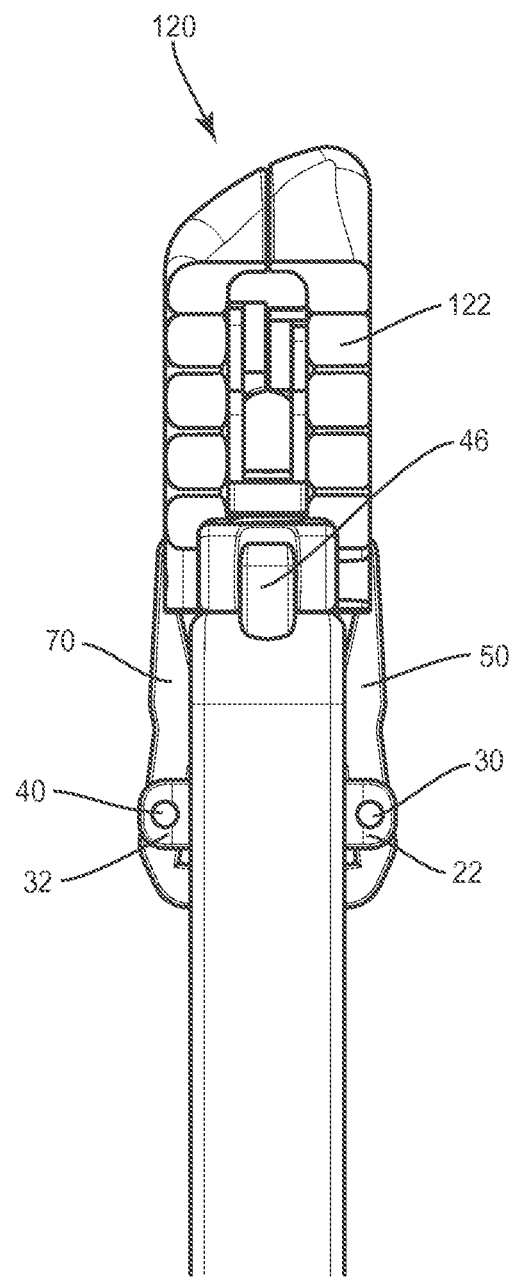
FIG. 12 is a plan view of components of one embodiment of a spinal implant system in accordance with the principles of the present disclosure.
Figure 13:
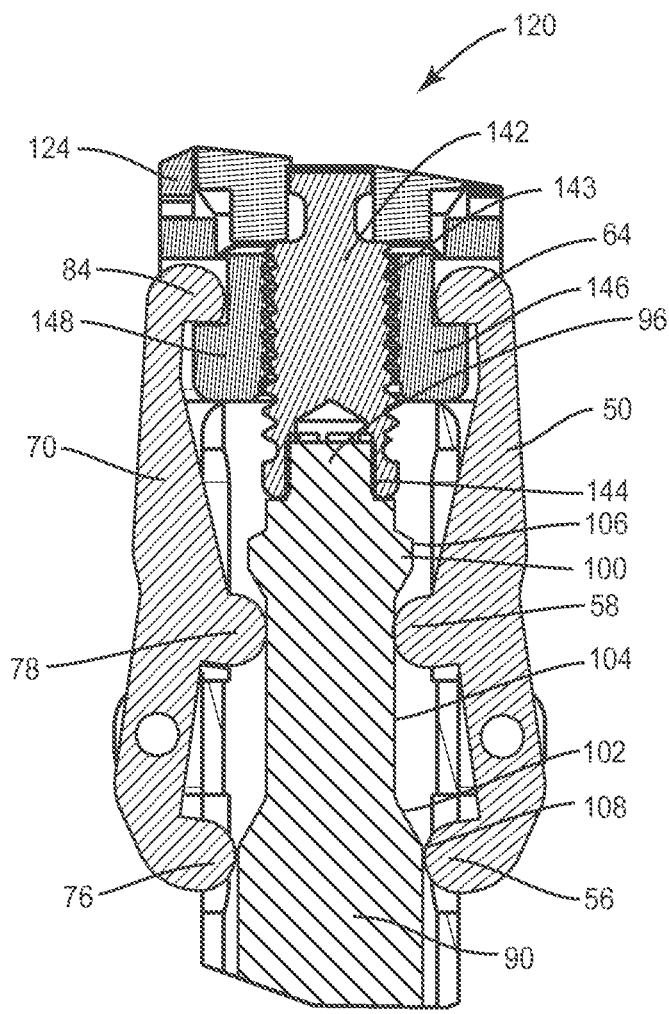
FIG. 13 is a cross section view of the components shown in FIG. 12.
Figure 14:
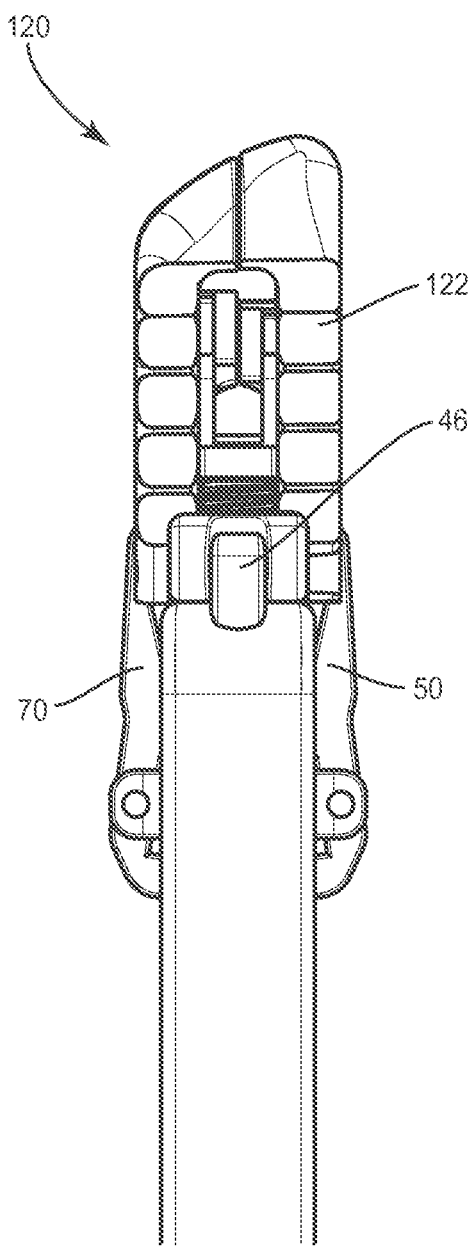
FIG. 14 is a plan view of components of one embodiment of a spinal implant system in accordance with the principles of the present disclosure.
Figure 15:
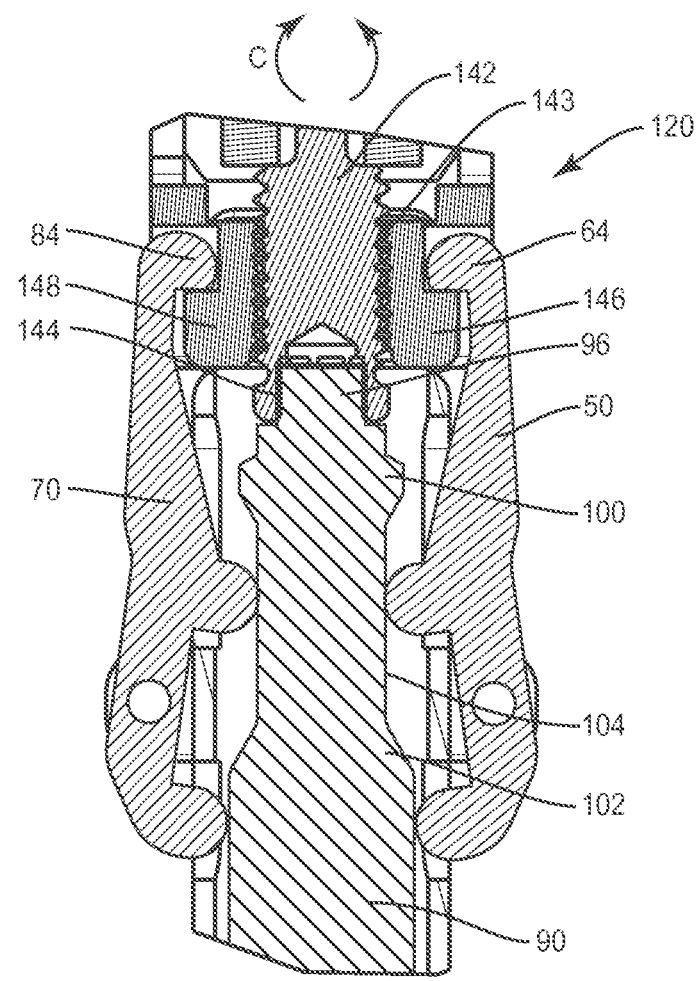
FIG. 15 is a cross section view of the components shown in FIG. 14.
Figure 16:
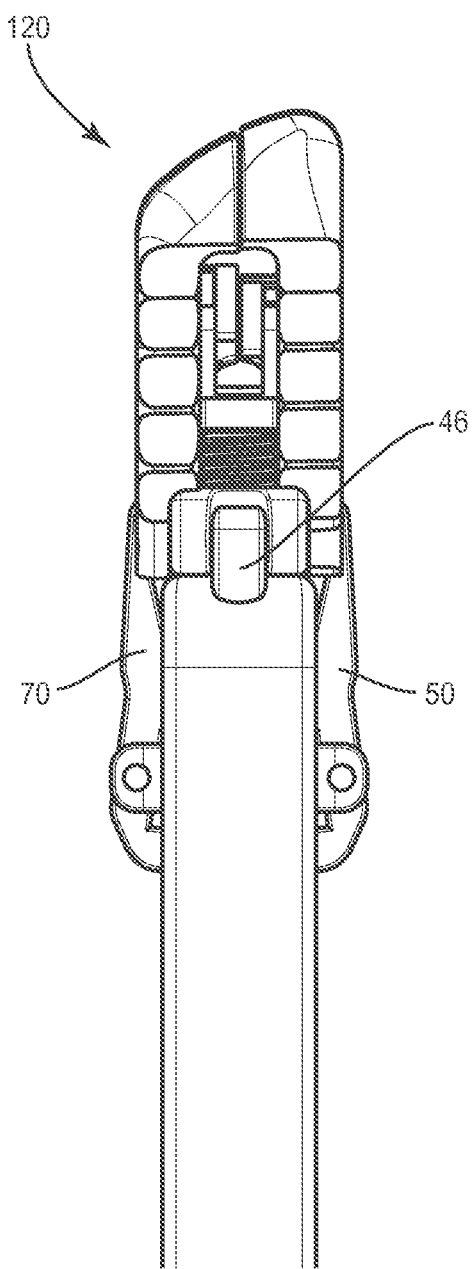
FIG. 16 is a plan view of components of one embodiment of a spinal implant system in accordance with the principles of the present disclosure.

Projections 56, 76 translate along ramp 102 to apex 108, as shown in FIG. 11. Translation of drive rod 90 and engagement of ramp 102 with projections 56, 76 cause arms 50, 70 to rotate about pins 30, 40, in a direction shown by arrows B in FIG. 11, into engagement with interbody implant 120. Rotation of arms 50, 70 causes hooks 64, 84 to engage interbody implant 120, as shown in FIG. 13, such that arms 50, 70 are releasably fixed in a locked orientation with interbody implant 120. Rotation of arms 50, 70 positions projections 58, 78 adjacent surface 104 into a position for engagement with ramp 100, as described herein. Upon engagement of arms 50, 70 with interbody implant 120, drive rod 90 engages a threaded shaft 143 of interbody implant 120, as described herein. Drive rod 90 is rotated, as shown by arrows C in FIG. 15, to cause threaded shaft 143 to actuate actuator 142 for expansion and/or contraction of interbody implant 120.

Figure 17:
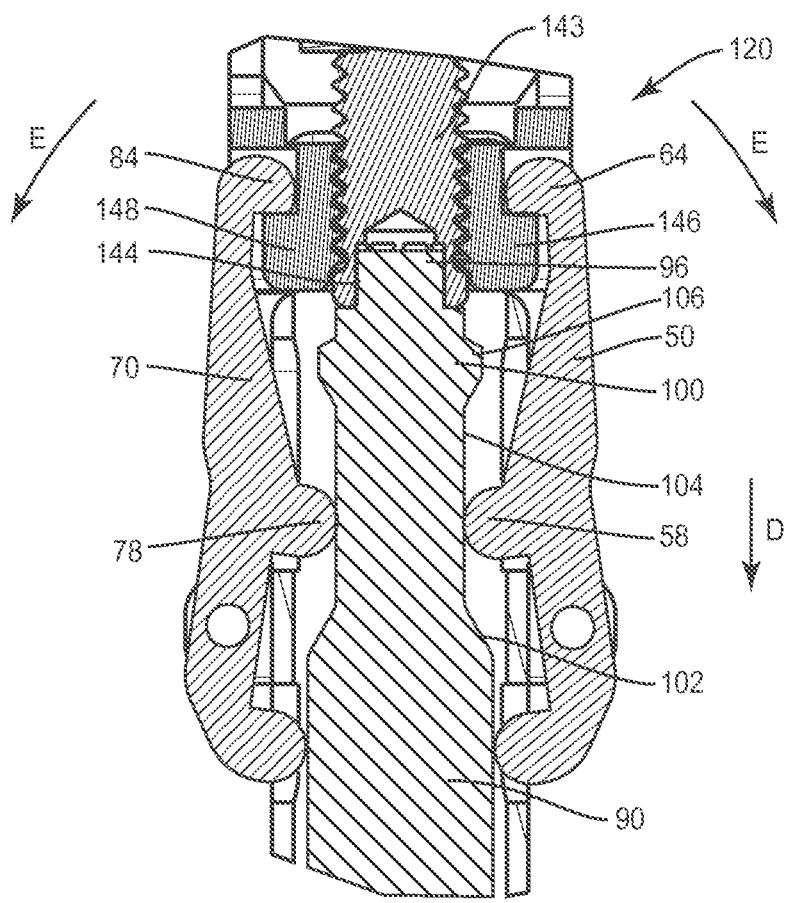
FIG. 17 is a cross section view of the components shown in FIG. 16.
Figure 18:
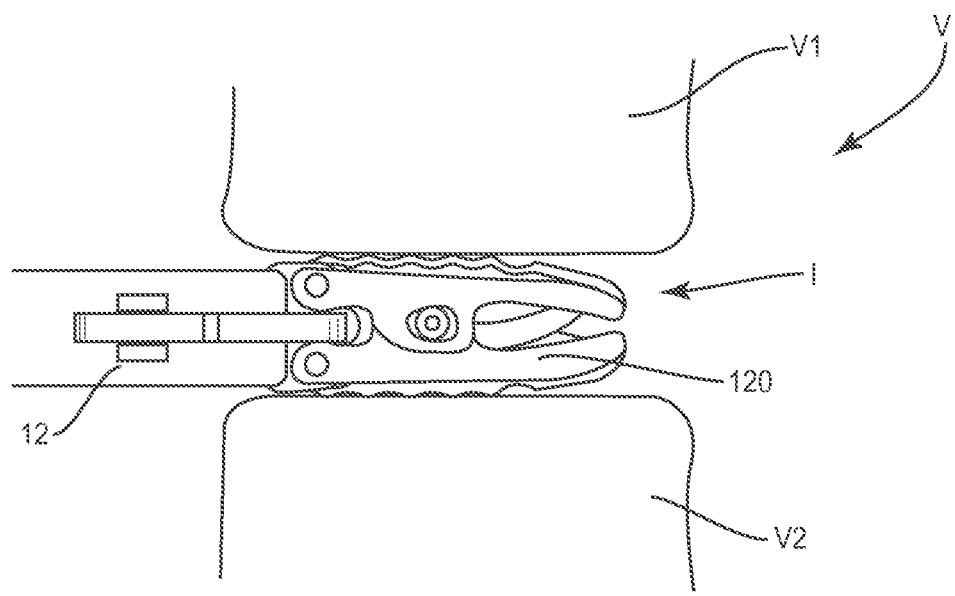
FIG. 18 is a perspective view of components of one embodiment of a spinal implant system in accordance with the principles of the present disclosure disposed with vertebrae.

In some embodiments, arms 50, 70 disengage from interbody implant 120 to a non-locked orientation. Drive rod 90 translates, in a direction shown by arrow D in FIG. 17, to be spaced from interbody implant 120 and disengages from threaded shaft 143. Translation of drive rod 90 in the opposite direction causes projections 58, 78 to translate along surface 104 such that ramp 100 slidably engages projections 58, 78. Ramp 100 slidably engages projections 58, 78 such that projections 58, 78 translate over apex 106 to bias arms 50, 70 for rotation, about pins 30, 40, in a direction shown by arrows E in FIG. 17. Rotation of arms 50, 70 causes hooks 64, 84 to disengage from interbody implant 120 into the non-locked orientation.

Interbody implant 120 includes a member 122 and a member 124. Member 122 extends between a surface 126 and a vertebral engaging surface 128. In some embodiments, the cross-sectional geometry of member 122 may have various configurations, such as, for example, round, oval, oblong, triangular, polygonal having planar or arcuate side portions, irregular, uniform, non-uniform, consistent, variable, horseshoe shape, U-shape or kidney bean shape. In some embodiments, surfaces 126, 128 may be smooth, even, rough, textured, porous, semi-porous, dimpled and/or polished.

Member 124 extends between a surface 130 and a vertebral engaging surface 132. In some embodiments, the cross-sectional geometry of member 124 may have various configurations, such as, for example, round, oval, oblong, triangular, polygonal having planar or arcuate side portions, irregular, uniform, non-uniform, consistent, variable, horseshoe shape, U-shape or kidney bean shape. In some embodiments, surfaces 130, 132 may be smooth, even, rough, textured, porous, semi-porous, dimpled and/or polished. In some embodiments, members 122, 124 can include one or more openings configured to receive an agent, which may include bone graft (not shown) and/or other materials for employment in a fixation or fusion treatment, as described herein.

Surfaces 126, 130 define a cavity 140. Cavity 140 is configured for moveable disposal of an actuator 142. Actuator 142 includes a threaded shaft 143. Drive rod 90 is configured to engage a portion, such as, for example, a socket 144 disposed at an end of threaded shaft 143. In some embodiments, socket 144 includes a hexalobe geometry configured for disposal of a similarly shaped engagement portion 96 of drive rod 90. In some embodiments, socket 144 has a cruciform, phillips, square, hexagonal, polygonal or star cross sectional configuration, configured for disposal of a correspondingly shaped portion of engagement portion 96. Engagement of drive rod 90 with threaded shaft 143 is configured to actuate actuator 142 to expand and/or contract interbody implant 120 for engagement with vertebral tissue, as described herein.

Surfaces 126, 130 define mating elements, such as, for example, hooks 146, 148. Hooks 146, 148 matingly engage hooks 64, 84 and define openings for disposal of hooks 64, 84 to facilitate engagement and retention of interbody implant 120 with surgical instrument 12. In some embodiments, hooks 146, 148 may extend transverse and/or at other angular orientations such as acute or obtuse, co-axial and/or may be offset or staggered relative to each other. In some embodiments, hooks 146, 148 form a friction fit and/or interference fit with hooks 64, 84. In some embodiments, hooks 146, 148 are flexible.

Surface 128 includes a mating element 150 engageable with projection 46. Mating element 150 includes a cavity configured for disposal of projection 46 of surgical instrument 12. Surface 132 includes a mating element 152 engageable with projection 46. Mating element 152 includes a cavity configured for disposal of projection 46 of surgical instrument 12. Engagement of projections 46 with mating elements 150, 152 is configured to stabilize a connection between instrument 12 and interbody implant 120. Engagement of protections 46 with mating elements 150, 152 is configured to facilitate engagement and disengagement of arms 50, 70 with interbody implant 120.

Referring to FIGS. 6-18, in assembly, operation and use, spinal implant system 10, similar to the systems and methods described herein, is employed with a surgical procedure, such as, for example, a fusion treatment of a spine of a patient including vertebrae V, intervertebral disc space I and body areas adjacent thereto, as discussed herein. In some embodiments, one or all of the components of spinal implant system 10 can be delivered or implanted as a pre-assembled device or can be assembled in situ. In some embodiments, one or all of the components of spinal implant system 10 may be completely or partially revised, removed or replaced.

For example, spinal implant system 10 can be employed with a surgical arthrodesis procedure, such as, for example, an interbody fusion for treatment of an applicable condition or injury of an affected section of a spinal column and adjacent areas within a body, such as, for example, intervertebral disc space I between a vertebra V1 and a vertebra V2 of vertebrae V. In some embodiments, spinal implant system 10 can include an intervertebral implant that can be inserted with intervertebral disc space I to space apart articular joint surfaces, provide support and maximize stabilization of vertebrae V. In some embodiments, spinal implant system 10 may be employed with one or a plurality of vertebra.

A medical practitioner obtains access to a surgical site including vertebrae V1, V2 such as through incision and retraction of tissues. Spinal implant system 10 can be used in any existing surgical method or technique including open surgery, mini-open surgery, minimally invasive surgery and percutaneous surgical implantation, whereby vertebrae V is accessed through a mini-incision, or sleeve that provides a protected passageway to the area. In one embodiment, the components of spinal implant system 10 are delivered through a surgical pathway to the surgical site along a surgical approach into intervertebral disc space I.

A preparation instrument (not shown) is employed to remove disc tissue, fluids, adjacent tissues and/or bone, and scrape and/or remove tissue from endplate surfaces of vertebra V1 and/or endplate surface of vertebra V2. In some embodiments, the size of interbody implant 120 is selected after trialing. In some embodiments, interbody implant 120 is visualized by fluoroscopy and oriented before introduction into intervertebral disc space I.

Surgical instrument 12 is configured for attachment with interbody implant 120 such that arms 50, 70 are disposed in the non-locked orientation, as shown in FIGS. 6-9. Surgical instrument 12 is guided into contact with interbody implant 120 to align projections 46 with mating elements 150, 152. Projections 46 are engaged with mating elements 150, 152.

Arms 50, 70 are disposed in an initial non-locked orientation relative to interbody implant 120, as shown in FIG. 7. Drive rod 90 is translated in a direction toward interbody implant 120, as shown by arrow A in FIG. 8, to engage interbody implant 120 to bias arms 50, 70 into a locked orientation. Translation of drive rod 90 causes ramp 102 to slidably engage projections 56, 76 to bias arms 50, 70 for rotation, about pins 30, 40 into engagement with interbody implant 120 into the locked orientation. Projections 56, 76 translate along ramp 102 to engage apex 108, as shown in FIG. 11. Translation of drive rod 90 and engagement of ramp 102 with projections 56, 76 causes arms 50, 70 to rotate about pins 30, 40, in a direction shown by arrows B in FIG. 11, into engagement with interbody implant 120. Rotation of arms 50, 70 positions projections 58, 78 adjacent surface 104. Rotation of arms 50, 70 cause hooks 64, 84 to matingly engage hooks 146, 148, as shown in FIG. 13, such that arms 50, 70 are releasably fixed in the locked orientation with interbody implant 120.

In the locked orientation, engagement portion 96 of drive rod 90 is engaged with socket 144 of threaded shaft 143. Interbody implant 120, attached with surgical instrument 12, is inserted into intervertebral disc space I. Drive rod 90 is rotated in a direction shown by arrows C in FIG. 15 to cause threaded shaft 143 to rotate such that actuator 142 causes interbody implant 120 to expand and/or contract to facilitate positioning with vertebrae V1, V2.

Upon positioning of interbody implant 120 with vertebrae V1, V2, surgical instrument 12 is disengaged from interbody implant 120. To disengage surgical instrument 12 from interbody implant 120, drive rod 90 translates in a direction away from interbody implant 120, as shown by arrow D in FIG. 17. Translation of drive rod 90 in the opposite direction causes projections 58, 78 to translate along surface 104 such that ramp 100 slidably engages projections 58, 78. Ramp 100 slidably engages projections 58, 78 such that projections 58, 78 translate over apex 106 to bias arms 50, 70 for rotation, about pins 30, 40, in a direction shown by arrows E in FIG. 17. Rotation of arms 50, 70 causes hooks 64, 84 to disengage from the mating engagement with hooks 146, 148 into the non-locked orientation. Surgical instrument 12 is removed from the surgical site.

In some embodiments, interbody implant 120 provides a footprint that improves stability and decreases the risk of subsidence into tissue. In some embodiments, interbody implant 120 provides height restoration between vertebral bodies, decompression, restoration of sagittal and/or coronal balance and/or resistance of subsidence into vertebral endplates. In some embodiments, interbody implant 120 engages and spaces apart opposing endplate surfaces of vertebrae V1, V2 and is secured within a vertebral space to stabilize and immobilize portions of vertebrae V in connection with bone growth for fusion and fixation of vertebrae V1, V2.

In some embodiments, interbody implant 120 may engage only one endplate. Components of spinal implant system 10 including interbody implant 120 can be delivered or implanted as a pre-assembled device or can be assembled in situ. Components of spinal implant system 10 including interbody implant 120 may be completely or partially revised, removed or replaced in situ. In some embodiments, one or all of the components of spinal implant system 10 can be delivered to the surgical site via mechanical manipulation and/or a free hand technique.

In one embodiment, spinal implant system 10 includes a plurality of interbody implants 120. In some embodiments, employing a plurality of interbody implant 120 can optimize the amount of vertebral space that can be spaced apart such that the joint spacing dimension can be preselected. The plurality of interbody implants 120 can be oriented in a side by side engagement, spaced apart and/or staggered.

In some embodiments, spinal implant system 10 includes an agent, which may be disposed, packed, coated or layered within, on or about the components and/or surfaces of spinal implant system 10. In some embodiments, the agent may include bone growth promoting material, such as, for example, bone graft to enhance fixation of interbody implant 120 with vertebrae. In some embodiments, the agent may include one or a plurality of therapeutic agents and/or pharmacological agents for release, including sustained release, to treat, for example, pain, inflammation and degeneration.

In one embodiment, interbody implant 120 may include fastening elements, which may include locking structure, configured for fixation with vertebrae V1, V2 to secure joint surfaces and provide complementary stabilization and immobilization to a vertebral region. In some embodiments, locking structure may include fastening elements, such as, for example, rods, plates, clips, hooks, adhesives and/or flanges. In some embodiments, the components of spinal implant system 10 can be used with screws to enhance fixation. The components of spinal implant system 10 can be made of radiolucent materials such as polymers. Radiomarkers may be included for identification under x-ray, fluoroscopy, CT or other imaging techniques.

In some embodiments, the use of microsurgical and image guided technologies may be employed to access, view and repair spinal deterioration or damage, with the aid of spinal implant system 10. Upon completion of the procedure, the non-implanted components, surgical instruments and assemblies of spinal implant system 10 are removed and the incision is closed.

In one embodiment, as shown in FIGS. 19-22, surgical system 10, similar to the systems and methods described herein, includes a surgical instrument 212, similar to surgical instrument 12 described with regard to FIGS. 1-18 configured for connection with interbody implant 120, as described herein.

Surgical instrument 212 includes a handle (not shown) that is connected with a member, such as, for example, a tubular shaft 216. Shaft 216 extends between a proximal end 218 and a distal end 220. Shaft 216 defines a longitudinal axis L2. End 220 includes flanges 222, 224 that are connected to an arm 250, as described herein.

Flanges 222, 224 include openings 226, 228 configured to receive a pin 230. Pin 230 facilitates rotation of arm 250 about flanges 222, 224 to engage an implant, such as, for example, an interbody implant 120, as described herein.

In some embodiments, end 220 includes flanges 232, 234 that are connected to an arm 270, as described herein. Ranges 232, 234 include openings 236, 238 configured to receive a pin 240 configured to facilitate rotation of arm 270 about flanges 232, 234 to engage interbody implant 120, as described herein. Ranges 222, 224, 232, 234 extend perpendicularly from shaft 216.

Shaft 216 includes a surface 242 that defines a cavity 244. Cavity 244 is configured for disposal of a drive rod 290, as described herein. Cavity 244 is configured for movable disposal of drive rod 290, as described herein, to facilitate engagement with interbody implant 120.

Shaft 216 includes projections 246 disposed at end 220. Projections 246 are configured for engagement with mating elements of interbody implant 120, as described herein. Projections 246 extend from shaft 216. Engagement of projections 246 with interbody implant 120 stabilizes a connection between surgical instrument 212 and interbody implant 120. Engagement of projections 246 with interbody implant 120 facilitates engagement and disengagement of arms 250, 270 with interbody implant 120.

Arm 250 extends between an end 252 and an end 254. End 252 includes projections 256, 258 configured for slidable engagement with ramps 300, 302, as described herein, to facilitate rotation of arm 250 between a locked orientation and a non-locked orientation with interbody implant 120, as described herein. Projections 256, 258 extend from arm 250. Projection 256 is engageable with ramp 302 to bias arm 250 relative to shaft 216 and/or drive rod 290 in a direction into a locked orientation and projection 258 is engageable with ramp 300 to bias arm 250 relative to shaft 216 and/or drive rod 290 in an opposite direction into a non-locked orientation.

End 252 includes an opening 262 configured for disposal of pin 230, as described herein, to facilitate rotation of arm 250 relative to shaft 216. In some embodiments, opening 262 is disposed intermediate or at a midpoint between projections 256, 258. End 254 includes a hook 264. Hook 264 extends from arm 250. Hook 264 is configured for engagement with interbody implant 120 to facilitate insertion and orientation of interbody implant 120 at a surgical site.

Arm 270 extends between an end 272 and an end 274. End 272 includes projections 276, 278 configured for slidable engagement with ramps 300, 302, as described herein, to facilitate rotation of arm 270 between a locked orientation and a non-locked orientation with interbody implant 120, as described herein. Projections 276, 278 extend from arm 270. Projection 276 is engageable with ramp 302 to bias arm 270 relative to shaft 216 and/or drive rod 290 in a direction into a locked orientation and projection 278 is engageable with ramp 300 to bias arm 270 relative to shaft 216 and/or drive rod 290 in an opposite direction into a non-locked orientation.

End 272 includes an opening 282 configured for disposal of pin 240, as described herein, to facilitate rotation of arm 270 relative to shaft 216. In some embodiments, opening 282 is disposed intermediate or at a midpoint between projections 276, 278. End 274 includes a hook 284. Hook 284 extends from arm 270. Hook 284 is configured for engagement with interbody implant 120 to facilitate insertion and orientation of interbody implant 120 at the surgical site.

Drive rod 290 includes a part, such as, for example, a tubular portion 292 and a part, such as, for example, a shaft 294. Shaft 294 is axially translatable relative to tubular portion 292, as described herein. Tubular portion 292 includes a surface 296. Surface 296 includes ramps, such as, for example, a ramp 300 and a ramp 302. Ramp 300 is oriented in spaced apart relation relative to ramp 302. An intermediate surface 304 is disposed between ramp 300 and ramp 302. Surface 304 is substantially even and circumferentially disposed about tubular portion 292. Ramp 300 includes an apex 306. Ramp 302 includes an apex 308. Tubular portion 292 is configured for movable disposal with cavity 244. In some embodiments, tubular portion 292 is configured for axial translation within cavity 244 to bias arms 250, 270 between a non-locked orientation and a locked orientation.

Tubular portion 292 includes a surface 298 that defines a channel 316. Channel 316 is configured for movable disposal of shaft 294, as described herein. In some embodiments, shaft 294 is configured for axial translation within channel 316 relative to tubular portion 292 and/or interbody implant 120.

Shaft 294 extends between an end 320 and an end 322. End 320 is configured for engagement with an actuator, such as, for example, a surgical driver (not shown). End 322 includes an engagement portion 324 configured to engage a portion of interbody implant 120 to facilitate expansion and contraction of interbody implant 120, as described herein. In some embodiments, shaft 294 is configured for engagement with interbody implant 120 to stabilize the connection of surgical instrument 212 with interbody implant 120. In some embodiments, engagement portion 324 includes a configuration, such as, for example, triangular, square, polygonal, hexalobular, star or torx. Shaft 294 is configured to axially translate within channel 316 for engagement with interbody implant 120 to bias arms 250, 270 between a non-locked orientation and a locked orientation.

Figure 19:
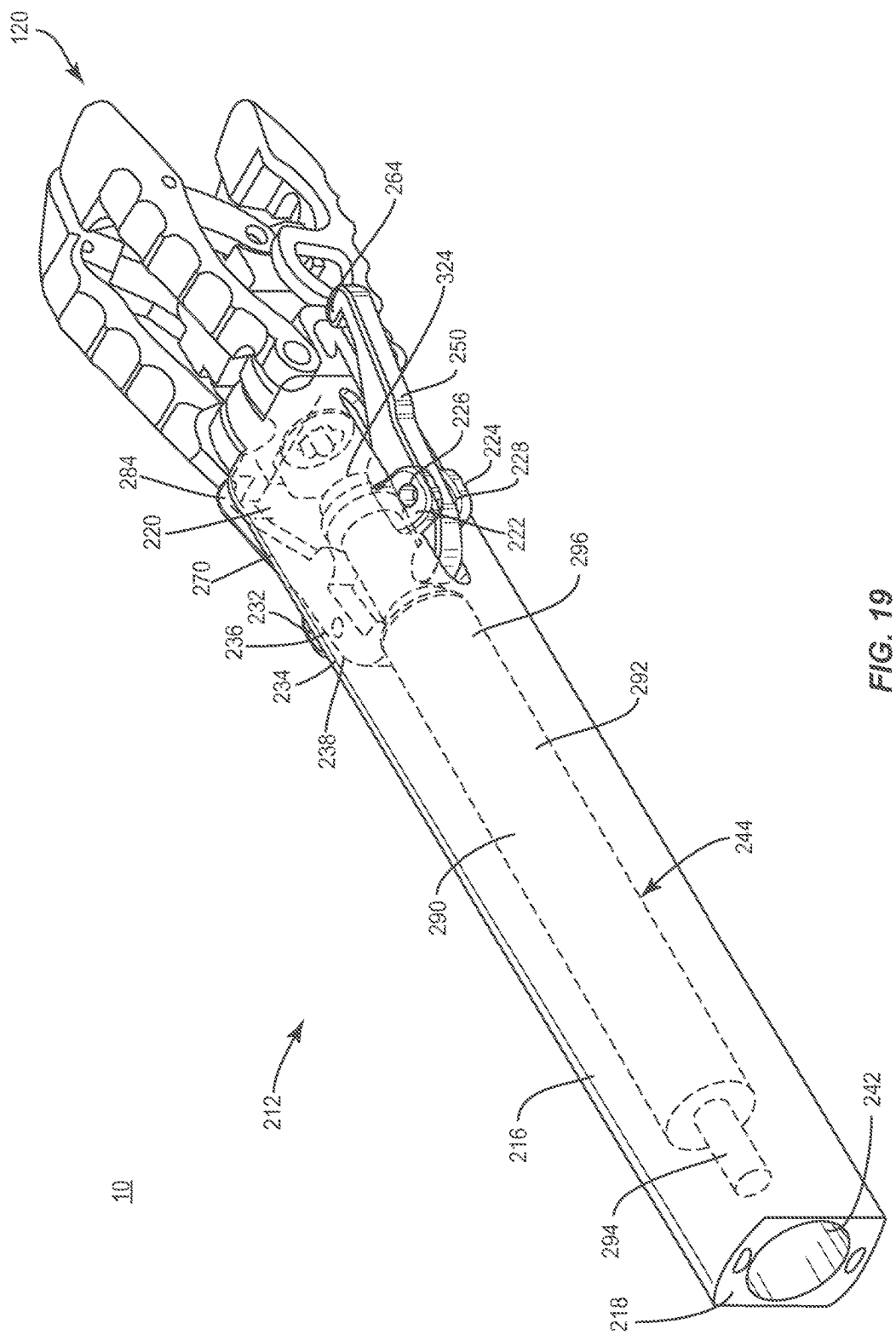
FIG. 19 is a break away perspective view, in part phantom, of components of one embodiment of a spinal implant system in accordance with the principles of the present disclosure.
Figure 20:
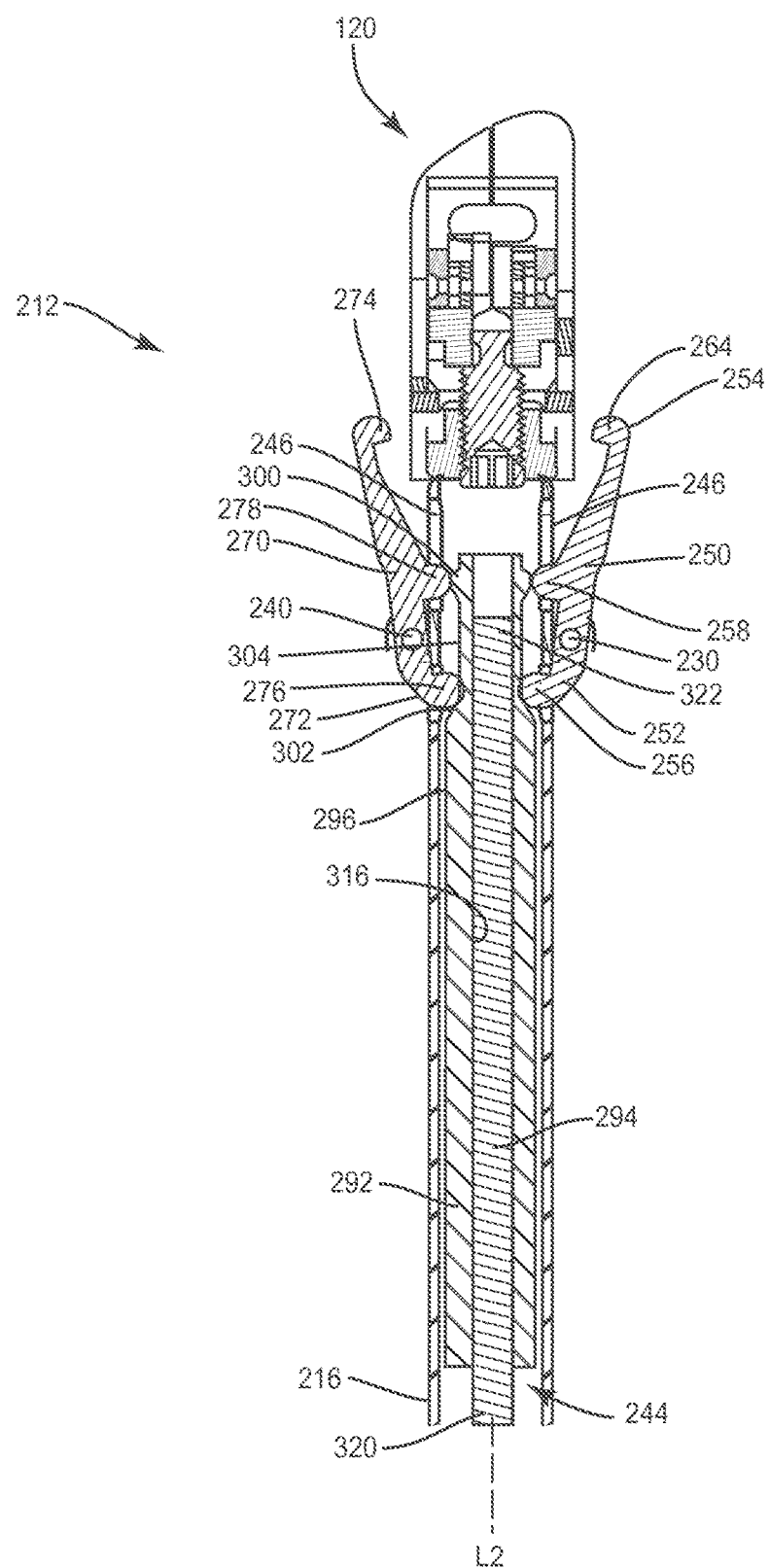
FIG. 20 is a cross section view of the components shown in FIG. 19.
Figure 21:
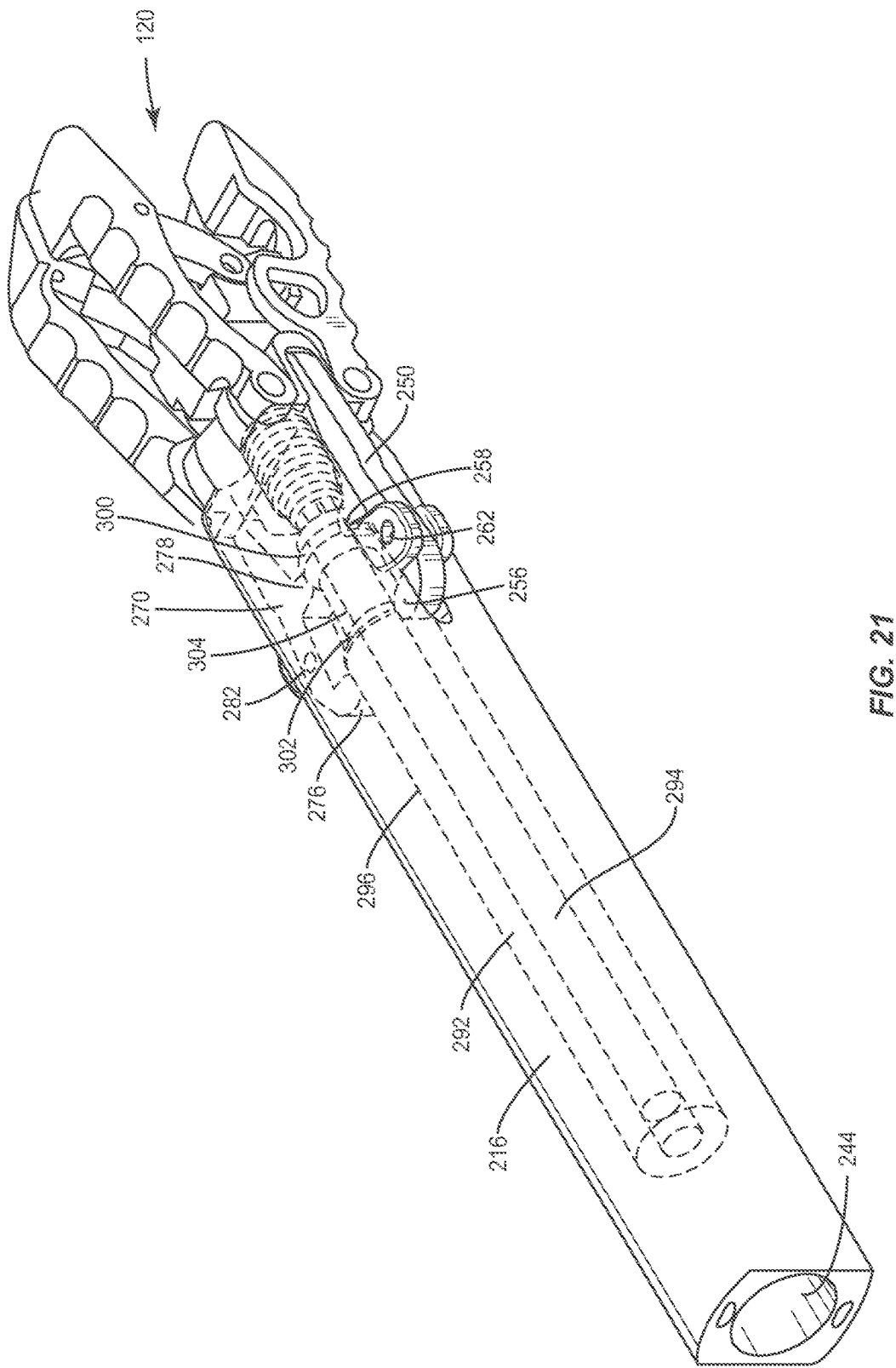
FIG. 21 is a perspective view, in part phantom, of the components shown in FIG. 19.
Figure 22:
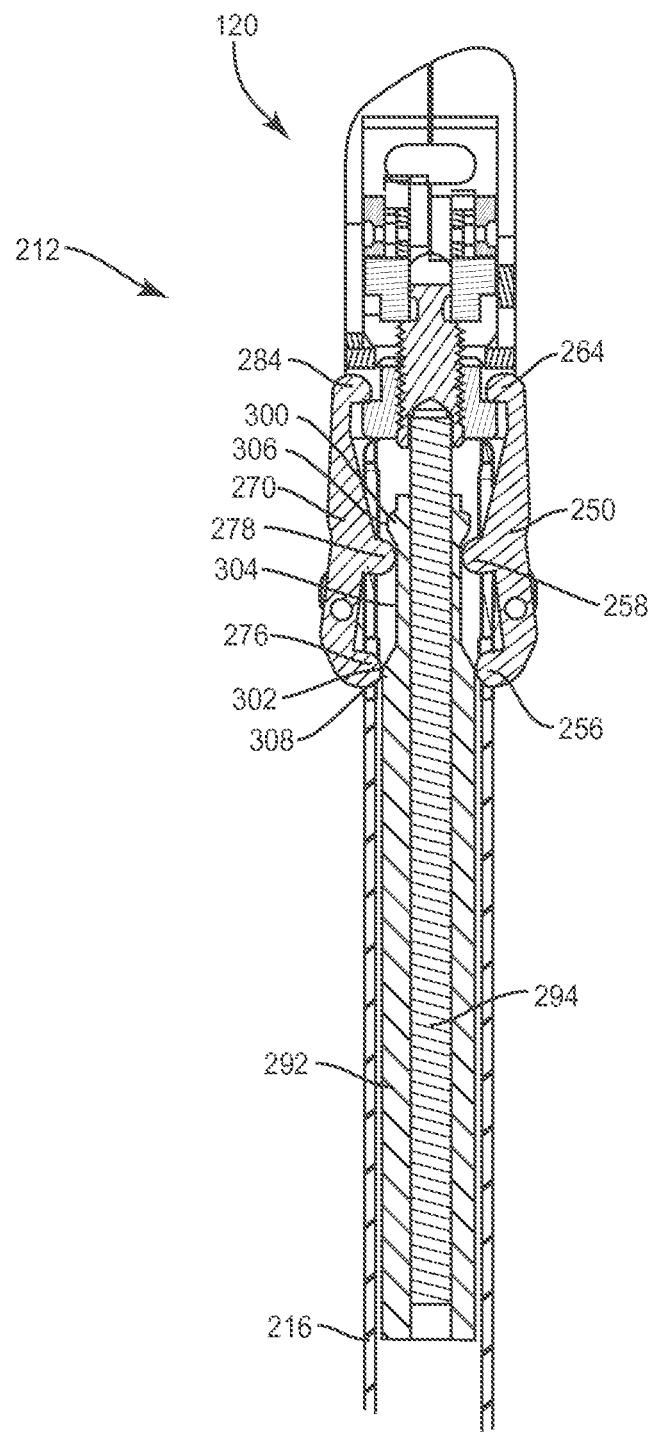
FIG. 22 is a cross section view of the components shown in FIG.
Figure 23:
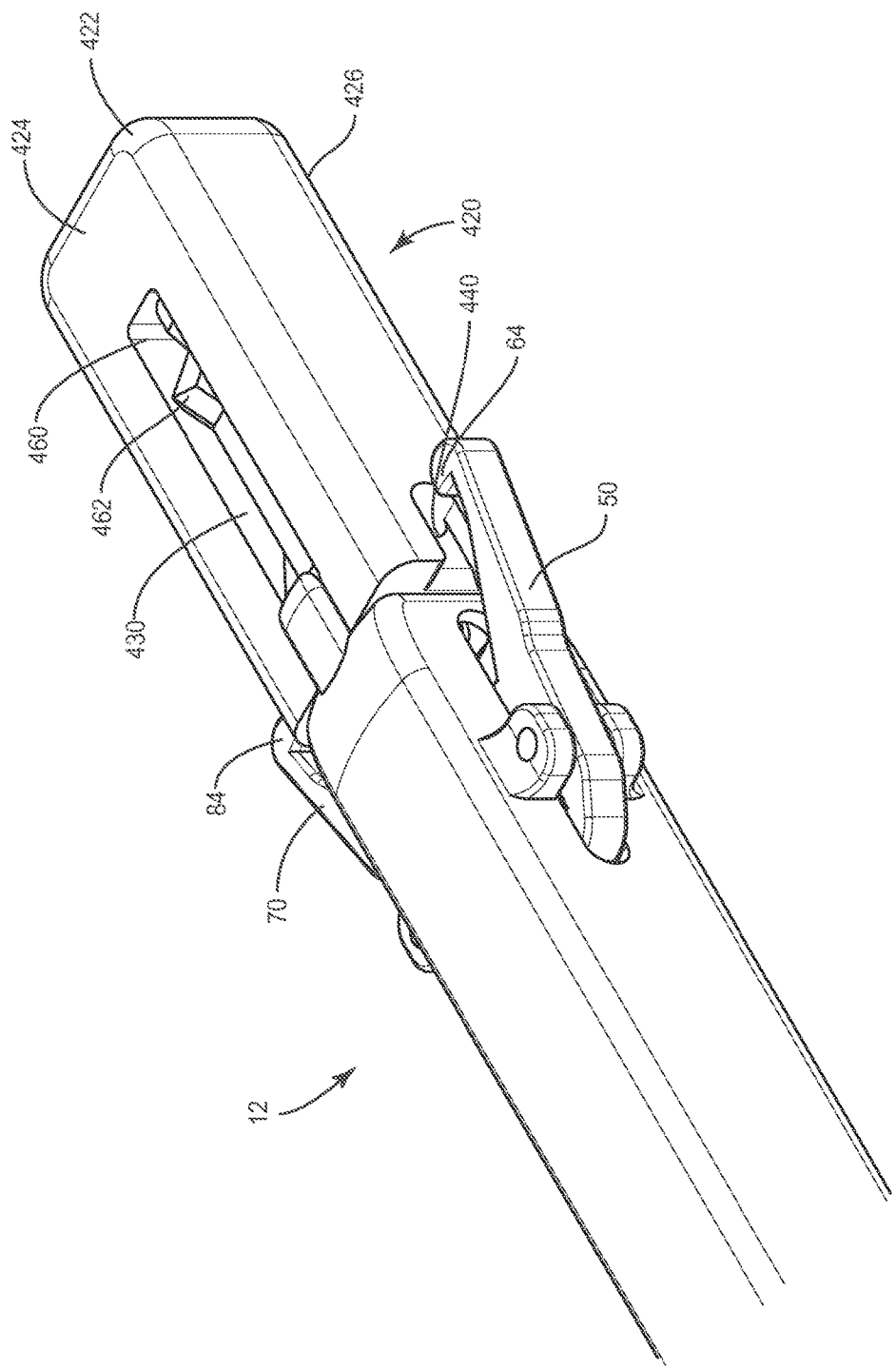
FIG. 23 is a break away perspective view of components of one embodiment of a spinal implant system in accordance with the principles of the present disclosure.
Figure 24:
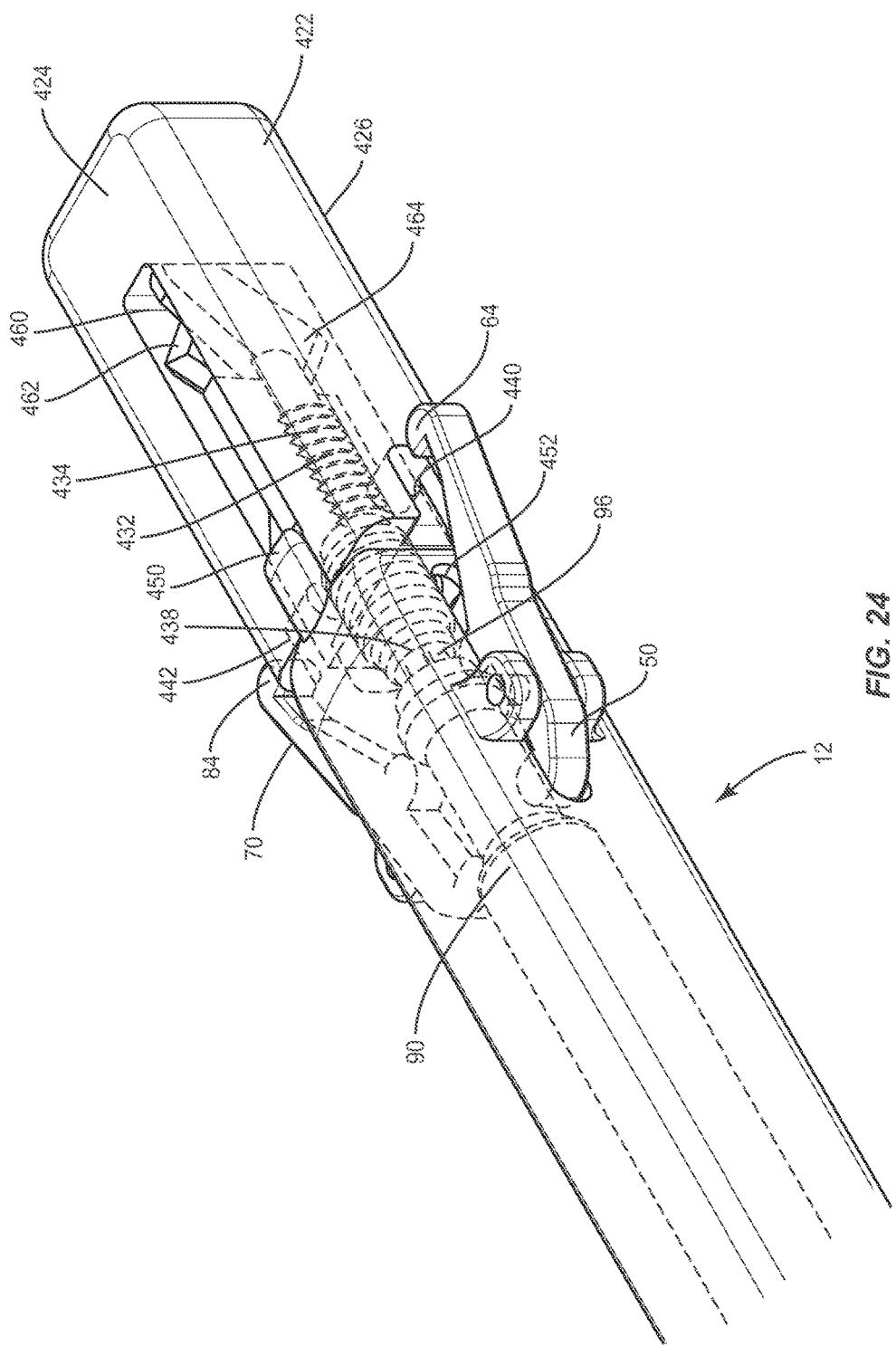
FIG. 24 is a perspective view, in part phantom, of the components shown in FIG. 23.
Figure 25:
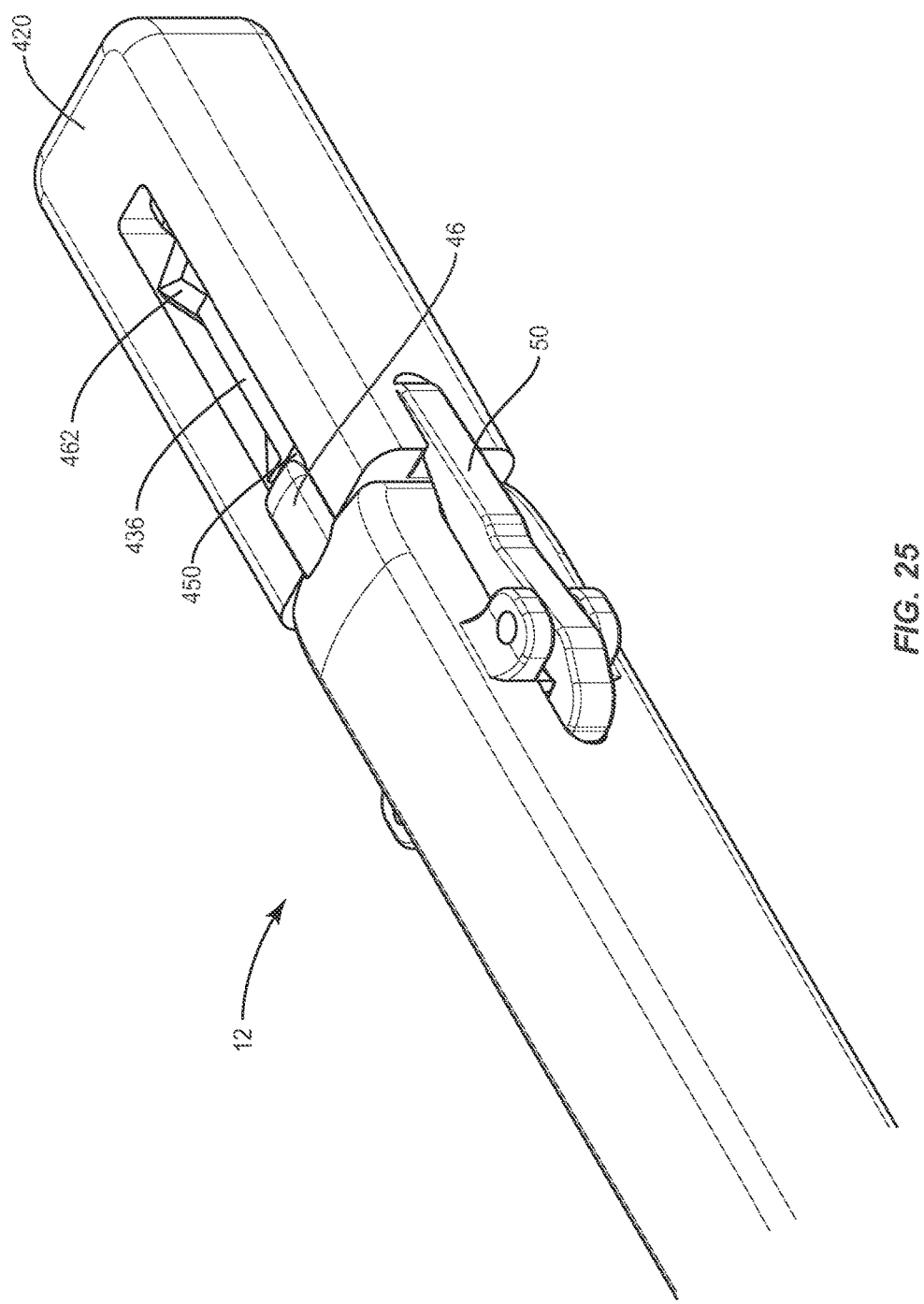
FIG. 25 is a perspective view of the components shown in FIG. 23.
Figure 26:
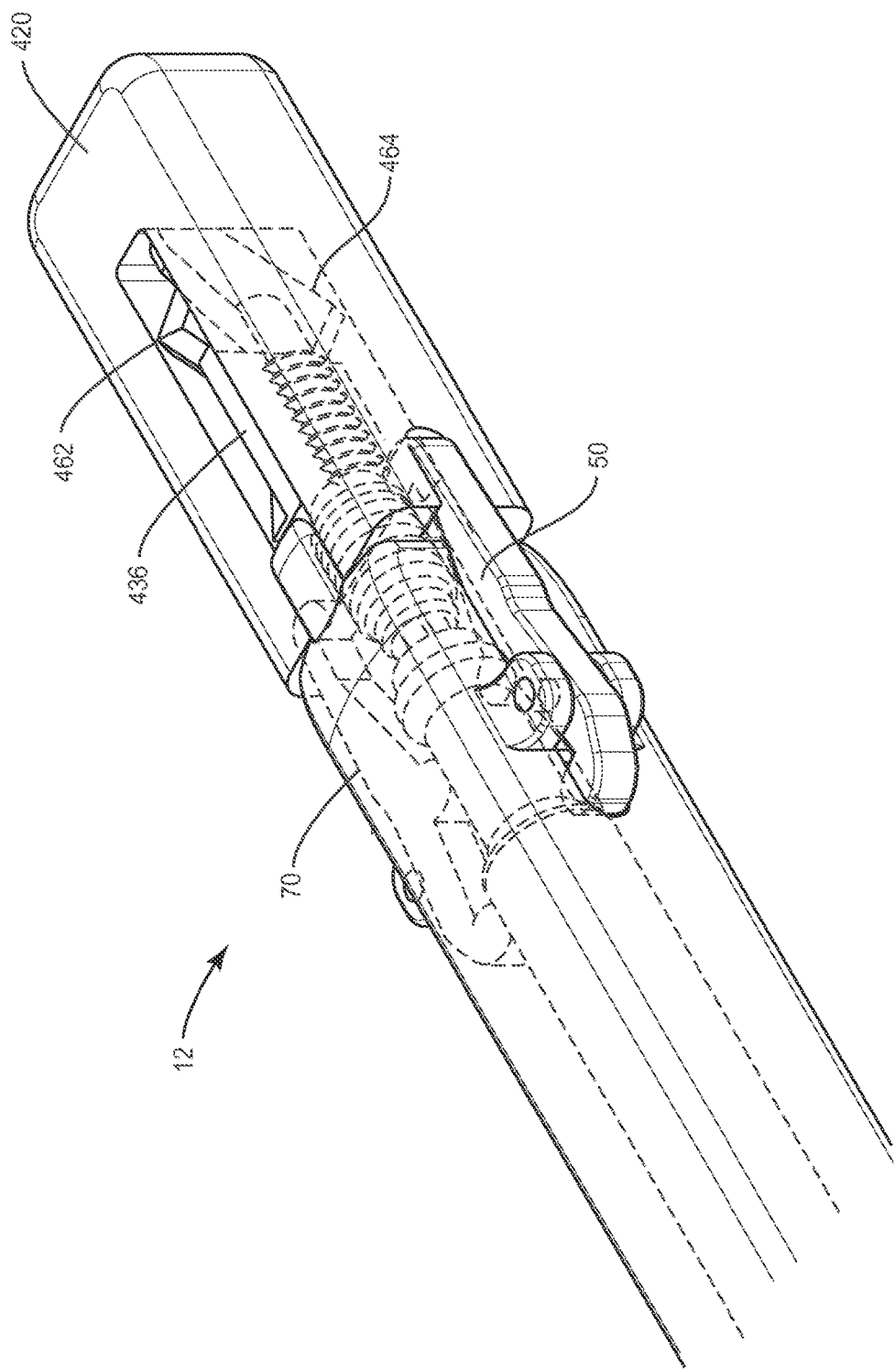
FIG. 26 is a perspective view, in part phantom, of the components shown in FIG. 23.

In some embodiments, drive rod 290 is initially disposed in a retracted orientation such that end 322 is disposed in tubular portion 292, as shown in FIGS. 19 and 20. Arms 250, 270 are disposed in a non-locked orientation with interbody implant 120. Shaft 294 is translated in a direction towards interbody implant 120 to engage end 322 with interbody implant 120, as shown in FIGS. 21 and 22 and similar to that described herein.

Tubular portion 292 is translated in a direction towards interbody implant 120 and ramp 302 slidably engages projections 256, 276 to bias arms 250, 270 for rotation, about pins 230, 240 into engagement with interbody implant 120 and into a locked orientation. Shaft 294 is rotatable to actuate expansion of interbody implant 120 between a contracted configuration and an expanded configuration, as described herein. In some embodiments, as tubular portion 292 translates in a direction away from interbody implant 120, ramp 300 slidably engages projections 258, 278 to bias arms 250, 270 for rotation, about pins 230, 240 to disengage from interbody implant 120 into the non-locked orientation.

In one embodiment, as shown in FIGS. 23-30, surgical system 10, similar to the systems and methods described herein, includes surgical instrument 12, as described herein, configured for connection with an implant 420. In some embodiments, implant 420 may be employed with surgical instrument 212 described herein.

Interbody implant 420 includes a member 422. Member 422 extends between a vertebral engaging surface 424 and a vertebral engaging surface 426. In some embodiments, the cross-sectional geometry of member 422 may have various configurations, such as, for example, round, oval, oblong, triangular, polygonal having planar or arcuate side portions, irregular, uniform, non-uniform, consistent, variable, horseshoe shape, U-shape or kidney bean shape. In some embodiments, surfaces 424, 426 may be smooth, even, rough, textured, porous, semi-porous, dimpled and/or polished.

Surfaces 424, 426 define a cavity 430. Cavity 430 is configured for moveable disposal of an actuator 432. Actuator 432 includes a threaded shaft 434 and a wedge 436. Wedge 436 includes a ramp 436a and ramp 436b. Ramps 436a, 436b are configured to engage fixation elements, as described herein, to move the fixation elements between a contracted orientation and an expanded orientation.

Drive rod 90, as described herein, is configured to engage a portion, such as, for example, a socket 438 disposed at an end of threaded shaft 434. In some embodiments, socket 438 includes a hexalobe geometry configured for disposal of a similarly shaped engagement portion 96 of drive rod 90, as described herein. In some embodiments, socket 438 has a cruciform, phillips, square, hexagonal, polygonal or star cross sectional configuration, configured for disposal of a correspondingly shaped portion of engagement portion 96. Engagement of drive rod 90 with threaded shaft 434 actuates actuator 432 to expand and/or contract a portion of implant 420, such as, for example, the fixation elements of implant 420, for engagement with vertebral tissue, as described herein.

Surfaces 424, 426 define mating elements, such as, for example, hooks 440, 442. Hooks 440, 442 matingly engage hooks 64, 84 and define openings for disposal of hooks 64, 84, as described herein, to facilitate engagement and retention of implant 420 with surgical instrument 12, similar to that described with regard to FIGS. 1-18. In some embodiments, hooks 440, 442 may extend transverse and/or at other angular orientations such as acute or obtuse, co-axial and/or may be offset or staggered relative to each other. In some embodiments, hooks 440, 442 form a friction fit and/or interference fit with hooks 64, 84. In some embodiments, hooks 440, 442 are flexible.

Surface 424 includes a mating element 450 engageable with projection 46. Mating element 450 includes a cavity configured for disposal of projection 46 of surgical instrument 12. Surface 426 includes a mating element 452 engageable with projection 46. Mating element 452 includes a cavity configured for disposal of projection 46 of surgical instrument 12. Engagement of projections 46 with mating elements 450, 452 is configured to stabilize a connection between instrument 12 and interbody implant 420. Engagement of protections 46 with mating elements 450, 452 is configured to facilitate engagement and disengagement of arms 50, 70 with interbody implant 420.

Member 422 includes a cavity 460. In some embodiments, cavity 460 is configured for disposal of a portion of implant 420. In some embodiments, implant 420 includes fixation elements, such as, for example, spikes 462, 464. Spikes 462, 464 are movably disposed with cavity 460. Spikes 462, 464 are configured for expansion and contraction within cavity 460 by actuation of actuator 432.

Figure 27:
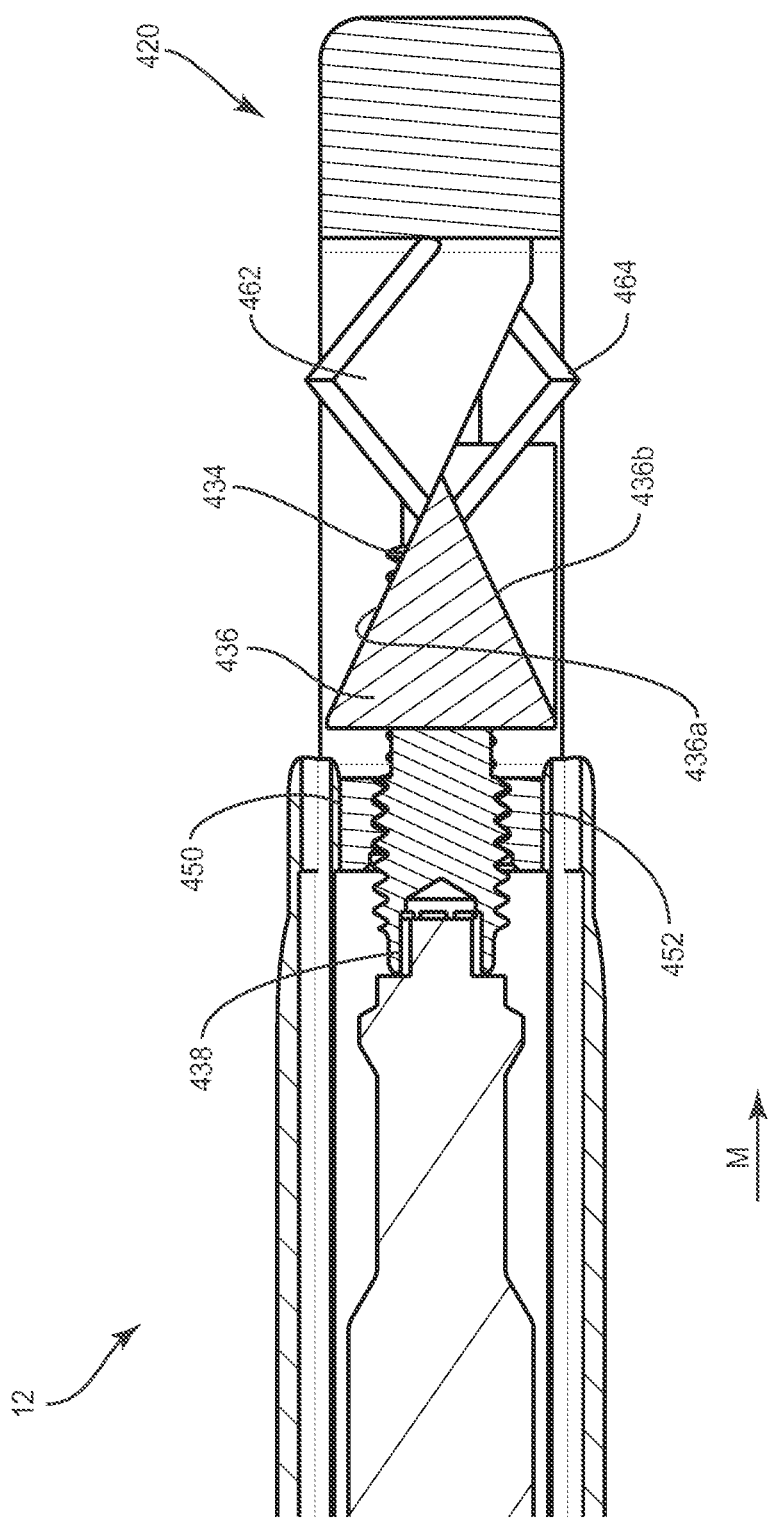
FIG. 27 is a cross section view of the components shown in FIG. 23.
Figure 28:
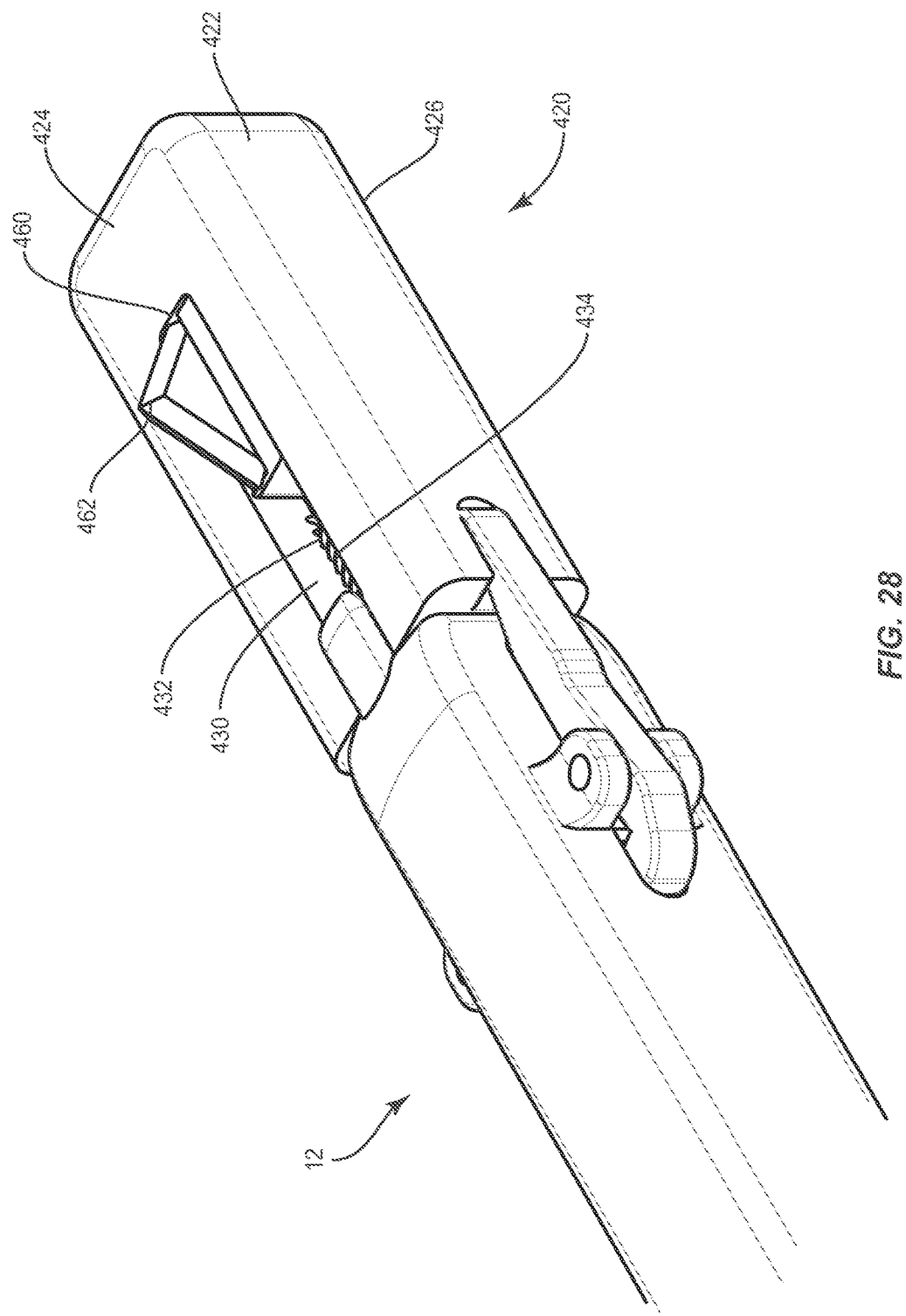
FIG. 28 is a perspective view of the components shown in FIG. 23.
Figure 29:
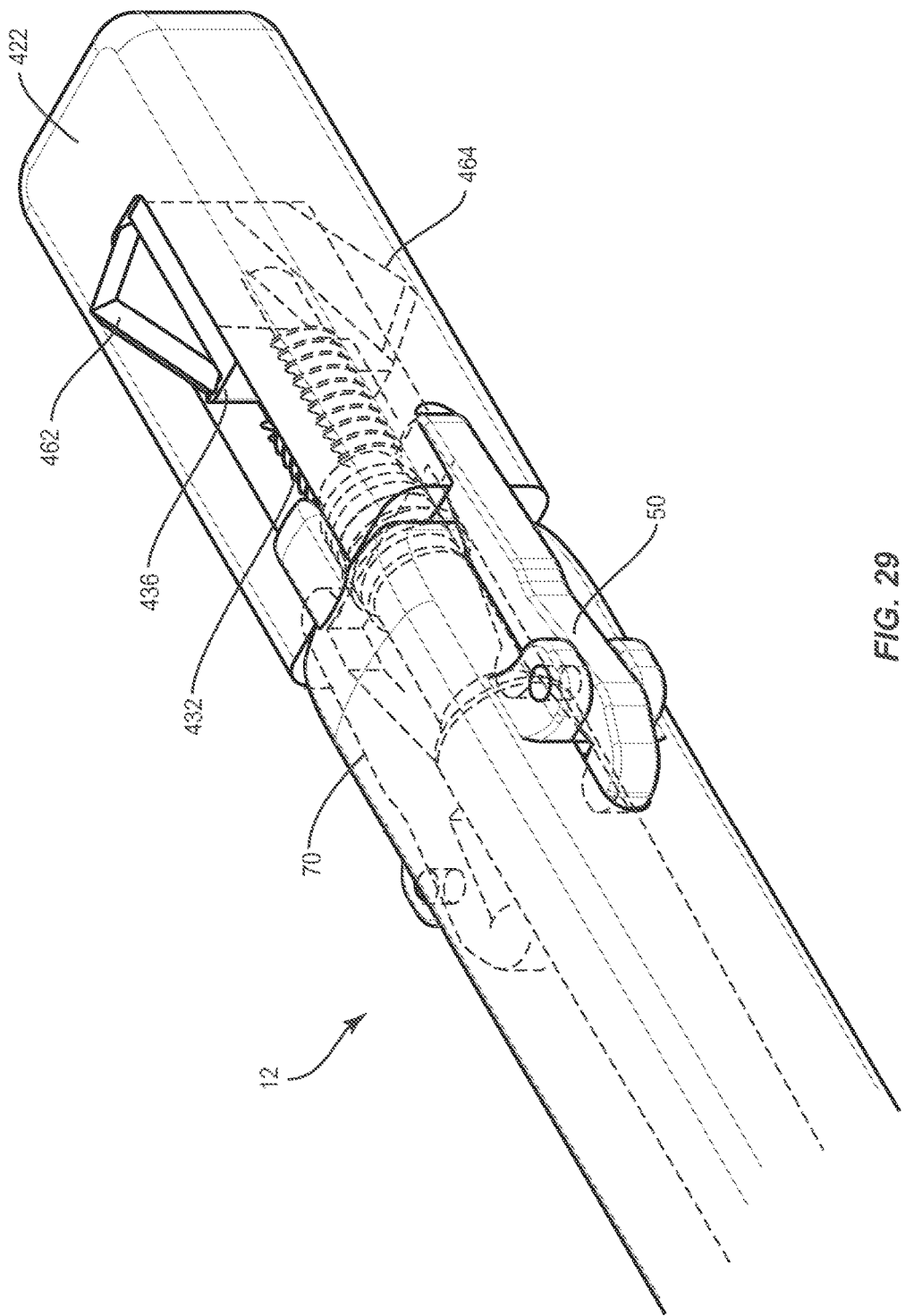
FIG. 29 is a perspective view, in part phantom, of the components shown in FIG. 23.
Figure 30:
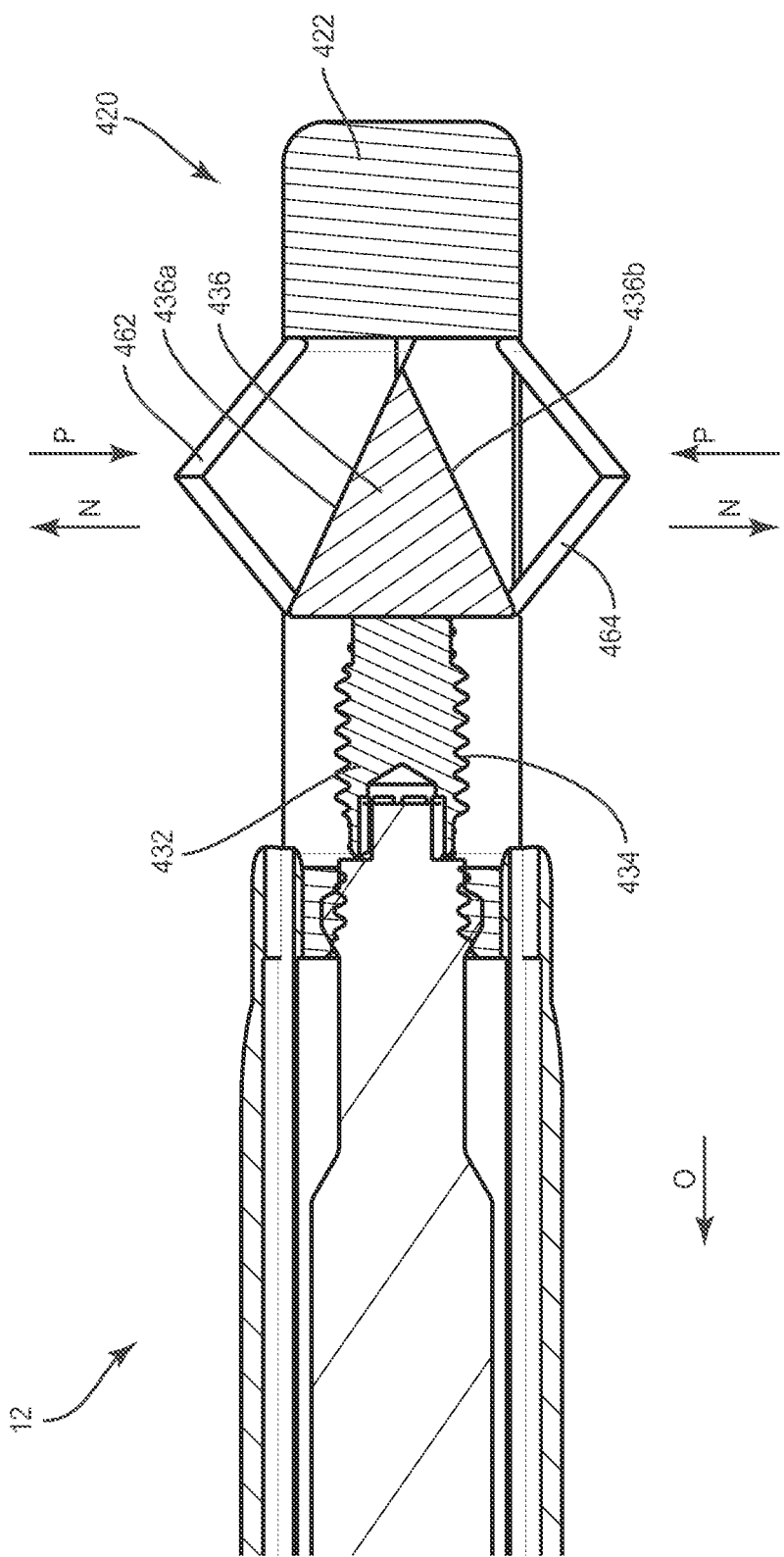
FIG. 30 is a cross section view of the components shown in FIG. 23.

Actuator 432 translates, in a direction shown by arrow M in FIG. 27, such that ramps 436a, 436b engage spikes 462 464. As such, wedge 436 causes spikes 462, 464 to expand relative to implant 420, in a direction shown by arrows N in FIG. 30. In some embodiments, spikes 462, 464 are expanded into engagement with vertebral tissue. In some embodiments, actuator 432 translates, in a direction shown by arrow O in FIG. 30, such that ramps 436a, 436b cause spikes 462, 464 to contract and/or collapse relative to implant 420, in a direction shown by arrows P in FIG. 30.

In some embodiments, implant 420 includes a member 422 that is non-expandable. In some embodiments, implant 420 comprises an expandable interbody implant, which includes one or more members that are expandable, similar to the systems and methods described with regard to FIGS. 1-18. In some embodiments, surgical instrument 12 is configured to expand and/or contract at least a portion, such as, for example, fixation elements of implant 420 between a first and a second configuration, and/or between a contracted or collapsed configuration and an expanded configuration, to activate a lock mechanism connected with the implant.

It will be understood that various modifications may be made to the embodiments disclosed herein. Therefore, the above description should not be construed as limiting, but merely as exemplification of the various embodiments.

Those skilled in the art will envision other modifications within the scope and spirit of the claims appended hereto.

What is claimed is:

1. A surgical instrument comprising:
    a first member;
    at least one lock; and
    a second member including at least one ramp that is translatable relative to the first member to engage and rotate the at least one lock relative to the first member between a locked orientation and a non-locked orientation with an interbody implant,
    the second member being engageable with the interbody implant to move at least a portion of the interbody implant between a contracted configuration and an expanded configuration.

2. A surgical instrument as recited in claim 1, wherein the first member includes a tubular shaft having an inner surface that defines a cavity configured for movable disposal of the second member.

3. A surgical instrument as recited in claim 1, wherein the first member extends between a proximal end and a distal end including a pivot, the at least one lock being connected to the pivot.

4. A surgical instrument as recited in claim 1, wherein the first member includes a mating element comprising at least one projection engageable with a mating element of the interbody implant.

5. A surgical instrument as recited in claim 1, wherein the at least one lock includes a rotatable arm connected with the first member, the arm having a mating element engageable with a mating element of the interbody implant in the locked orientation.

6. A surgical instrument as recited in claim 1, wherein the second member includes a first part and a second part movable relative to the first part.

7. A surgical instrument as recited in claim 1, wherein the at least one lock includes a rotatable arm connected with the first member, the arm having a first projection engageable with the at least one ramp to bias the arm to the locked orientation and a second projection engageable with the at least one ramp to bias the arm to the non-locked orientation.

8. A surgical instrument as recited in claim 1, wherein the at least one lock includes a first rotatable arm and a second rotatable arm connected with the first member, the first arm being rotatable in a first direction relative to the first member and the second arm being rotatable in a second, opposite direction relative to the first member.

9. A surgical instrument as recited in claim 1, wherein the interbody implant includes at least one fixation element and the second member engages the interbody implant to move the at least one fixation element between a contracted configuration and an expanded configuration.

10. A surgical instrument as recited in claim 1, wherein the second member is axially translatable and rotatable relative to the first member.

11. A surgical instrument as recited in claim 1, wherein the second member is rotatable relative to the first member to actuate the interbody implant between a contracted configuration and an expanded configuration.

12. A surgical instrument as recited in claim 1, wherein the second member includes a hexalobular drive element engageable with the interbody implant.

13. A surgical instrument as recited in claim 1, wherein the at least one ramp includes a first ramp and a second ramp spaced apart from the first ramp.

14. A surgical instrument as recited in claim 1, wherein the at least one ramp includes a first ramp and a second ramp, the first ramp being engageable with the at least one lock to bias the at least one lock to the locked orientation and the second ramp being engageable with the at least one lock to bias the at least one lock to the non-locked orientation.

15. A surgical instrument comprising:
    a tubular shaft;
    a first rotatable arm connected with the shaft;
    a second rotatable arm connected with the shaft; and
    a drive rod translatable relative to the shaft and including at least one ramp that is translatable relative to the shaft to engage and rotate the arms relative to the shaft between a capture orientation and a release orientation with an interbody implant,
    the rod being engageable with the interbody implant to move at least a portion of the interbody implant between a contracted configuration and an expanded configuration.

* * * * *

UNITED STATES PATENT AND TRADEMARK OFFICE
CERTIFICATE OF CORRECTION

PATENT NO. : 10,188,526 B2  
APPLICATION NO. : 14/923190  
DATED : January 29, 2019  
INVENTOR(S) : Adriaan J. Kuyler It is certified that error appears in the above-identified patent and that said Letters Patent is hereby corrected as shown below:

In the Specification

In Column 1, Line 3, delete "HELD" and insert -- FIELD --, therefor.

In Column 1, Line 65, delete "FIG." and insert -- FIG. 1; --, therefor.

In Column 2, Line 39, delete "FIG." and insert -- FIG. 21; --, therefor.

In Column 5, Line 17, delete "dements" and insert -- elements --, therefor.

In Column 5, Lines 45-46, delete "Ranges 32, 34" and insert -- Flanges 32, 34 --, therefor.

In Column 5, Line 49, delete "Ranges 22, 24, 32, 34" and insert -- Flanges 22, 24, 32, 34 --, therefor.

In Column 11, Line 58, delete "Ranges 232, 234" and insert -- Flanges 232, 234 --, therefor.

In Column 11, Line 61, delete "Ranges 222, 224, 232, 234" and insert -- Flanges 222, 224, 232, 234 --, therefor.

Signed and Sealed this  
Twenty-third Day of April, 2019

Andrei Iancu  
*Director of the United States Patent and Trademark Office*